US011516987B2

(12) United States Patent
Eckard et al.

(10) Patent No.: US 11,516,987 B2
(45) Date of Patent: Dec. 6, 2022

(54) ***BACCATUM CYTOPLASMIC* MALE STERILITY WITH FEMALE FERTILE FLOWERS IN *CAPSICUM ANNUUM***

(71) Applicant: Seminis Vegetable Seeds, Inc., St. Louis, MO (US)

(72) Inventors: Jonathan T. Eckard, St. Louis, MO (US); Maria L. Hop, St. Louis, MO (US); Patrick Hogan, St. Louis, MO (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 0 days.

(21) Appl. No.: 16/453,748

(22) Filed: Jun. 26, 2019

(65) Prior Publication Data

US 2020/0015446 A1 Jan. 16, 2020

Related U.S. Application Data

(60) Provisional application No. 62/690,722, filed on Jun. 27, 2018.

(51) Int. Cl.

| | |
|---|---|
| ***A01H 5/08*** | (2018.01) |
| ***A01H 6/82*** | (2018.01) |
| ***C12Q 1/6895*** | (2018.01) |
| ***A01H 5/10*** | (2018.01) |

(52) U.S. Cl.

CPC ............... *A01H 6/822* (2018.05); *A01H 5/08* (2013.01); *A01H 5/10* (2013.01); *C12Q 1/6895* (2013.01)

(58) Field of Classification Search

CPC ...................................................... A01H 6/822

See application file for complete search history.

(56) References Cited

U.S. PATENT DOCUMENTS

| | | | |
|---|---|---|---|
| 5,866,764 A | 2/1999 | Gabor et al. | |
| 6,096,944 A | 8/2000 | Vierling et al. | |
| 6,207,367 B1 | 3/2001 | Helentjaris et al. | |
| 6,414,226 B1 | 7/2002 | Hoogstraten | |
| 6,639,132 B1 | 10/2003 | Duvick et al. | |
| 9,642,318 B2 * | 5/2017 | Gorguet .................. | A01H 5/08 |
| 2017/0188535 A1 | 7/2017 | Gorguet et al. | |
| 2018/0171353 A1 | 6/2018 | Eckhard et al. | |
| 2020/0040357 A1 | 2/2020 | Eckard et al. | |

FOREIGN PATENT DOCUMENTS

WO 1991/002069 A1 2/1991

OTHER PUBLICATIONS

International Search Report and Written Opinion regarding PCT Application No. PCT/US2019/039178, dated Dec. 2, 2019.

International Search Report and Written Opinion regarding PCT Application No. PCT/US2019/039185, dated Nov. 26, 2019.

GenBank Accession No. AC211024, Sep. 26, 2007.

GenBank Accession No. JW144115, Sep. 1, 2007.

GenBank Accession No. HG975443, Nov. 19, 2015.

U.S. Appl. No. 16/453,757, filed Jun. 26, 2019, Eckard, et al.

Berke, "Hybrid Seed Production in Capsicum", Journal of New Seeds, (2000), 49-67, 1(3-4).

Dhaliwal and Jindal, "Induction and Exploitation of Nuclear and Cytoplasmic Male Sterility in Pepper (*Capsicum* spp.): a Review," Journal of Horticultural Science & Biotechnology, (2014), 471-479, 89(5).

Ishikawa, et al., "High ß-carotene and Capsaicinoid Contents in Seedless Fruits of 'Shishitoh' Pepper," HortScience: a publication of the American Society for Horticultural Science, (2004), 153-155, 39(1).

Jo, et al., "Fine Mapping of Restorer-of-Fertility in Pepper (*Capsicum annuum* L.) Identified a Candidate Gene Encoding a Pentatricopeptide Repeat (PPR)-Containing Protein," Theoretical and Applied Genetics, (2016), 2003-2017, 129(10).

Kumar, et al., "Genetics and Distribution of Fertility Restoration Associated RAPD Markers in Inbreds of Pepper (*Capsicum annuum* L.)," Scientia Horticulturae, (2007), 197-202, 111(3).

Lin, et al., "Restorer Breeding in Sweet Pepper: Introgressing Rf Allele from Hotpepper through Marker-Assisted Backcrossing," Scientia Horticulturae, (2015), 170-175, 197.

Manzur, et al., "Successful Wide Hybridization and Introgression Breeding in a Diverse Set of Common Peppers (*Capsicum annuum*) Using Different Cultivated Aji (*C. baccatum*) Accessions as Donor Parents," PLoS ONE, (2015), 10(12).

Monteiro, et al., "Reproductive Characterization of Interspecific Hybrids Among *Capsicum* Species," Crop Breeding and Applied Biotechnology, (2011), 241-249, 11(3).

Mulyantoro, et al., "Conversion of the Genic Male Sterility (GMS) System of Bell Pepper (*Capsicum annuum* L.) to Cytoplasmic Male Sterility (CMS)," Plant Breeding, (2014), 291-297, 133(2).

Shifriss, "Male Sterility in Pepper (*Capsicum annuum* L.)," Euphytica, (1997), 83-88, 93(1).

Tiwari, et al., "Selection of Sweet Pepper (*Capsicum annuum* L.) Genotypes for Parthenocarpic Fruit Growth," Acta Hort. 761, ISHS, (2007), 135-140.

Invitation to Pay Additional Fees regarding PCT Application No. PCT/US2019/039178, dated Sep. 18, 2019, 4 pages.

Invitation to Pay Additional Fees regarding PCT Application No. PCT/US2019/039185, dated Sep. 18, 2019, 3 pages.

USPTO Response to Non-Final Office Action regarding U.S. Appl. No. 16/453,757, filed Jul. 12, 2021.

Swamy, et al. CMS system and its stimulation in hybrid seed production of *Capsicum annuum* L., Scientia Horticulturae 222:175-179, 2017.

USPTO: Restriction Requirement regarding U.S. Appl. No. 16/453,757, dated Dec. 30, 2020.

(Continued)

*Primary Examiner* — Russell Kallis

(74) *Attorney, Agent, or Firm* — Dentons US LLP; Matthew L. Madsen, Esq.

(57) ABSTRACT

The present disclosure provides *Capsicum annuum* BCMS plants exhibiting uniform female fertility. Such plants comprise novel introgressed genomic regions associated with uniform female fertility from *Capsicum annuum* on chromosome 6. In certain aspects, compositions and methods for producing, breeding, identifying, and selecting plants or germplasm with a uniform female fertility phenotype are provided.

21 Claims, 4 Drawing Sheets

Specification includes a Sequence Listing.

(56) References Cited

OTHER PUBLICATIONS

USPTO: Response to Restriction Requirement regarding U.S. Appl. No. 16/453,757, filed Jan. 13, 2021.
USPTO: Non-Final Office Action regarding U.S. Appl. No. 16/453,757, dated Apr. 27, 2021.
USPTO: Final Office Action regarding U.S. Appl. No. 16/453,757, dated Nov. 9, 2021.
USPTO: Response to Final Office Action regarding U.S. Appl. No. 16/453,757, filed Jan. 7, 2022.
USPTO: Supplemental Response to Final Office Action regarding U.S. Appl. No. 16/453,757, filed May 9, 2022.
USPTO: Advisory Action regarding U.S. Appl. No. 16/453,757, dated Feb. 22, 2022.
USPTO: Examiner-Initiated Interview Summary regarding U.S. Appl. No. 16/453,757, dated Feb. 22, 2022.
USPTO: Notice of Allowance regarding U.S. Appl. No. 16/453,757, dated Jun. 29, 2022.

* cited by examiner

| Marker | *C. baccatum* map (cM) | *C. annuum* map (cM) |
|---|---|---|
| M17 | 0 | 25.7 |
| M22 | 0 | 30.2 |
| **Gf** | **0** | **N/A** |
| M33 | 1.3 | 40.8 |
| M36 | 1.3 | 48.9 |
| M43 | 3.4 | 57.4 |
| M44 | 48.4 | 81.3 |
| M45 | 54.8 | 89.3 |
| M46 | 61.8 | 94.8 |
| M47 | 73.7 | 107.4 |
| M48 | 106.2 | 118.8 |
| M49 | 119.7 | 132.4 |
| M50 | 120.7 | 134.6 |
| M51 | 122.3 | 137.3 |

| Marker | Phenotype | Genotype (cytoplasm/genome) | |
|---|---|---|---|
| | | bacc/ann | ann/ann |
| **M20 (6.1 cM)** | Good flower | **108** | 0 |
| | Bad flower | 0 | **88** |
| **M10 (0.15 cM)** | Good flower | **109** | 0 |
| | Bad flower | 0 | **88** |

FIG. 2

| Recurrent parent | | | C. baccatum parent | C. annuum control | Line 1 | Line 2 | Line 3 | Line 4 | Line 5 | Line 6 | Line 7 | Line 8 | Line 9 | Line 10 | Line 11 | Line 12 | Line 13 | Line 14 | Line 15 | Line 16 | Line 17 | Line 18 |
|---|---|---|---|---|---|---|---|---|---|---|---|---|---|---|---|---|---|---|---|---|---|---|
| % *C. annuum* | | | 0.0% | 100.0% | 99.8% | 99.2% | 100.0% | >99.9% | >99.9% | >99.9% | 100.0% | >99.9% | >99.9% | 100.0% | >99.9% | >99.9% | 100.0% | >99.9% | >99.9% | 100.0% | >99.9% | 100.0% |
| Cytoplasm type | | | Bac | Ann | Bac | Bac | Ann | Bac | Bac | Bac | Ann | Bac | Bac | Ann | Bac | Bac | Ann | Bac | Bac | Ann | Bac | Ann |
| Gf genotype | | | GfGf | gfgf | Gfgf | Gfgf | gfgf | gfgf | Gfgf | Gfgf | gfgf | Gfgf | Gfgf | gfgf | gfgf | Gfgf | gfgf | gfgf | Gfgf | gfgf | Gfgf | gfgf |
| Flower phenotype | | | Complete fertile | Complete fertile | Male sterile | Male sterile | Complete fertile | Complete sterile | Male sterile | Male sterile | Complete fertile | Male sterile | Male sterile | Complete fertile | Complete sterile | Male sterile | Complete fertile | Complete sterile | Male sterile | Complete fertile | Male sterile | Complete fertile |
| Marker | Position (cM) | Alleles | | | | | | | | | | | | | | | | | | | | |
| M8 | 0.1 | C/T | CC | TT | CT | CT | TT | TT | CT | CT | TT | CT | CT | TT | TT | CT | TT | TT | CT | TT | CT | TT |
| M13 | 1.9 | A/G | GG | AA | AG | AG | GG | GG | GG | GG | AA | AG | AG | AA | AA | AG | AA | AA | AG | AA | AG | AA |
| M2 | 1.9 | A/G | GG | AA | GG | GG | AA | AA | AG | AG | -- | GG | GG | GG | GG | GG | -- | GG | GG | -- | GG | GG |
| M19 | 5.8 | C/T | CC | TT | CC | CC | TT | TT | CT | CT | TT | CT | CT | CC | CC | CC | CC | CC | CC | TT | CT | CC |
| M20 | 6.1 | A/G | GG | AA | AG | AG | GG | GG | GG | GG | GG | GG | GG | AA | AA | AG | AA | AA | AG | GG | GG | AA |
| M16 | 6.2 | A/G | AA | GG | AA | AA | GG | GG | AG | AG | GG | AG | AG | AA | AA | AA | AA | AA | AA | GG | AG | AA |
| M18 | 6.2 | A/C | AA | CC | AC | AC | AA | AA | AA | AA | AA | AA | AA | CC | CC | AC | CC | CC | AC | AA | AA | CC |
| M22 | 7.8 | A/T | AA | TT | AA | AA | TT | TT | AT | AT | AA | AA | AA | AA | AA | AA | AA | AA | AA | AA | AA | AA |
| M25 | 14.7 | A/G | AA | GG | AG | -- | GG | GG | AG | AG | GG | AG | AG | GG | GG | AG | GG | GG | AG | GG | AG | GG |
| M35 | 26.7 | C/T | CC | TT | CT | CT | TT | CT | CT | CT | CC | CC | CC | CC | CC | CC | TT | TT | CT | CC | CC | TT |
| M36 | 35.7 | C/G | GG | CC | CG | -- | CC | CC | CG | CG | CC | CG | CG | CC | CC | CG | CC | CC | CC | CC | CG | CC |
| M37 | | C/G | GG | CC | CG | CG | CC | CC | CG | CG | CC | CG | CG | CC | CC | CG | CC | CC | CC | CC | CG | CC |
| M38 | | A/T | TT | AA | AA | AA | AA | AA | AT | AT | AA | AT | AT | AA | AA | AA | AA | AA | AA | AA | AT | AA |
| M39 | | A/G | GG | AA | AA | AA | AA | AA | AA | AA | AA | AA | AG | AA | AA | AA | AA | AA | AA | AA | AG | AA |
| M40 | | A/G | AA | GG | GG | GG | GG | GG | GG | GG | -- | GG | GG | GG | GG | GG | -- | GG | GG | -- | GG | -- |
| M41 | | C/T | CC | TT | TT | TT | TT | TT | TT | TT | TT | TT | TT | TT | TT | TT | TT | TT | TT | TT | TT | TT |
| M42 | | A/T | AA | TT | TT | TT | TT | TT | TT | TT | TT | TT | TT | TT | TT | TT | TT | TT | TT | TT | TT | TT |

SEQUENCE LISTING

<160> NUMBER OF SEQ ID NOS: 36

<210> SEQ ID NO 1
<211> LENGTH: 1641
<212> TYPE: DNA
<213> ORGANISM: Capsicum baccatum

<400> SEQUENCE: 1
gaaatttgtt cttcttcttt cccttccttt tttgttttgg attttcctca ttgcaagtag 60
aaatgtctct aacggctatg gttttaatag ttcatccgag aagagagtta ctgctgttgc 120
catcagtaat gacggtcgtt ttgtagcttt cgcggataaa tttggtgtaa tttatgcagt 180
tgaaatagaa ggttatcatg aaaatcaaac tctgcccgat aagaaggcag tcccgattct 240
tgcccactat tgcagcatca ttactagtct ggtatgtttc tttcctttcc tcttcatgtg 300
aatttgcttt agttttcgat gagtcaattt ttgtatccta tatatatgag ggttagcagt 360
ttactcagat attgttacga tactcatgat ctatgttgct cgaactcttt aaaaatgcta 420
ttaggtgcat gtcggattct tcaaaagtag ggcatttttg gaggatccga cacgagtatg 480
gcaacatttt tggtgagtcg gagcaactta gctcatgatt ggtccttgta agcagttttc 540
tacggaaatt gtgttttcat atacactgtt ctggcaatgg cattcatcgc tcgactcttc 600
tacacaaata ttatggataa tgatctactg tctcgatgca catctcttgc acaatttgtt 660
gcaagcgttg tccatcctgc cagtcaagta taaagcgtta tctttctggt gactagacca 720
tgatactctt atcgtctatg attacttcat ataagattaa gtttagcgta ttcctagctc 780
gccatatcac ataacacttt ctctaccaaa ttagtttgat tccataatca aggcctcttg 840
tttcaaaagc tagttagttt ttgctcaaat aggattttcc atcttgcagg agttttcacc 900
tgacggacga tacgttatta gtgccgatcg agacttcaaa atccgagtaa tgtcatgctt 960
cttattaacc atgaatctta gtaagatttc ttgatgacct ccagctaaca tcaagatttc 1020
ttatgggtca taattacagg tctctgtgtt cccagaaaag ccatcagatg gagctcacga 1080
gattcaaagc ttttgccttg gccatacaga gtaagaattt cttgaaactt gggtggtccg 1140
aactccgaat accctcagtt ttgataatca agctgatcca gaatagtcgt tttctgttga 1200
aatgttggtt atactgctaa aattgttaaa atctagtgac agtttcttgt cattatcggt 1260
aaaagccaat cttgacattt gaccaggata agtcgaccag gacgatttag gttgtcattt 1320
tttgtgtcgt ccgacttgta catctgatta aattatctat accatgcaga aacagtgtcg 1380
ctggagcatt tttatgtgta ttttccgaat ttattctcct tttacacgtt ttataggtta 1440
gggaatctgg gtggtgcgga agtagacaat aacgaaagca aataaacagt gactaacgca 1500
aataaagaag acacaaattt tacgtggttc tattagttag acataatcct tgcgtgggag 1560
tggggggtgg ggatgtgcta ctgttagctg tgtttctacg tcggtaccct tgttgactta 1620
tctttttttg gatataaaaa a 1641

<210> SEQ ID NO 2
<211> LENGTH: 301
<212> TYPE: DNA
<213> ORGANISM: Capsicum baccatum
<220> FEATURE:
<221> NAME/KEY: misc_feature
<222> LOCATION: (211)..(211)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t

<400> SEQUENCE: 2
cacatgaaga ggaaaggaaa agaaacatac cagactagta atgatgctgc aatagtgggc 60
aagaatcggg actgccttct tatcgggcag agtttgattt tcatgataac cttctatttc 120

-continued

```
aactgcataa attacaccaa atttatccgc gaaagctaca aaacgaccgt cattactgat    180

ggcaacagca gtaactctct tctcggatga nctattaaaa ccatagccgt tagagacatn    240

tctacttgca atgaggaaaa tccaaaacaa aaaaaggaag ggaaagaaga agaacaaatt    300

t                                                                    301


<210> SEQ ID NO 3
<211> LENGTH: 301
<212> TYPE: DNA
<213> ORGANISM: Capsicum baccatum
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t

<400> SEQUENCE: 3

gaaatagcat cancaccaac aatgtgaacc tctncaggta ataaagtttc tgagaaagtc     60

caatgcaata agaagtgaaa agagcttgaa ttgtgatgca gggttgtgta atttacatca    120

ccaagaatca gccaccgata ancatttcga gatgagagac tgctgttttt aatgatcaac    180

agtaaaagtt gttcctaaga atgccanctc aaacttctag acaaaattgc tgcatatttc    240

cctcctgttt cttanaaaag aagttttatt tgagtaccat taggtaaatg gctataacct    300

a                                                                    301


<210> SEQ ID NO 4
<211> LENGTH: 2458
<212> TYPE: DNA
<213> ORGANISM: Capsicum baccatum

<400> SEQUENCE: 4

gaagattggt tcagtggctt ataagctctc acttccccat acgtcttttt tttttttgg     60

gatacggatt ttattcaaag agtaccaagg tggtagaaca aaaggtacat gacttagcaa    120

caaactctat aatccactac cacatattat ctcctagcaa gtacaaaagg ttcaaatact    180

tatccatcat atctaaagtg ctgctataac accaaaagta cagatttttt atacatttat    240

tttttactct agaaatgttt aacttcttcc catgaaagca tgacttgttt tctagccata    300

aggttcatat tatgcaattg ataatagttc tccgcattgg cttcaagcta cttcccccta    360

ggttgttgct tcaccaacca tttcatgtat ccctgttgaa gccttgctat gttgttccag    420

gcgtcattac acatcctcca gtagtggaca ttttcagtcc ttactgtccc aaacctgagt    480

aggtgttaga caagaggatg atccaaagag gcaataaggc cattgctcac gtgttcattc    540

agtgggagca cattcctgta gatcaggcta cgtgggagga cttcaatgca atcaagactc    600

gattctcttt gtttgttcct tgaggacgag aaagttttta atggaggagc attaatgtgt    660

tctggaatcg agaagcagaa ttatgcagaa aaaggtggta cgctaagttg gaggaggtgt    720
```

-continued

```
acttagtggt ctgcccatta gttattacgg ttaagcaaga gaaggcgtgg tgagagtgac    780

aaaaggccta atctgtctcc taagtggctc agggtcaatt cttgctagga atattccacc    840

ttctggtatt acattgggta tgctgttgtc gttttgctgt cattacagtt tttcccctt    900

acttttcaaa cacgggttag gttaatcgcg cattagccca tcttattggg cacttttgct    960

ccaattcctt tttggcatgt tcactcgtat atgtagttgc agagttccca ttcagactta   1020

tgaatcaaaa cccgtagcta tttccttctt cttttgtagt tagcttatta atccttcatc   1080

aattgctccg ttccaagctc gattgcatca aaactactgg aagttacaag taaatcagca   1140

gacattatga ttaaattcat tcatggccta aaaacctact agcttatgta aaaaaggtac   1200

gccatatata ctaacaatat ctgtaaacag ttacgacatc aatcaagcag gcgaagaaat   1260

tttattccta caaattcata ccttaaactg gttctggcgt tttctggctt tctctagttc   1320

ctgctcgaga tgagctgctt ctcgtttcaa ggttgagaaa tcttcctgca gtgagccctt   1380

ctccatctcc cgtgcttgac acttcttcag tatctcttgc tccctcgcaa cagcttggtg   1440

gaagtttgta gcagacccca gggcagccag cgttgcagcc tccaactctt tctttagcac   1500

agcattctcc acctcaagtc tgtgaagagt agagttagcc atctcaattt ggccgccggc   1560

atttgacaat gcatacccca tttcggagag cctcttcatg ttgcattctc cctgactttg   1620

cttttccttc tgaattttct cagcctcttc tttctcttgc cttagcattt taagctcccc   1680

ctggtccttg ccaagcctcc gagcagcctg cataaccttc tcattggccc aatcagtcca   1740

cccttggagc tctttctgca gtgtctgcat acgagaaatt agcaacaata tagtttcgtc   1800

tttctcattt tgtgggacat gtttccccaa agactcatcg tatgggatac cagtataata   1860

gtctagaaat ttaggagggg caggaatgct gcctggggcc tttgaggaag acttgggctc   1920

cggaactaga gatgcaggag tatttgtgtt aacagcaggc aacgcacaaa cagtatcttg   1980

ggtcgctggc ccactaccag tttcacttga aggtgcaacg gaggaggagg tgcatgaact   2040

atgagaacag cctccggcta aagggccatt gcttttaact gtattcgcta ccttagagta   2100

agtactcttc attacgagac cagaagaaca agattcagag ctcagcgtct tgtccaaaac   2160

catattgctc caggtggtga gttttgcttt aaaggaaccc ttactcatac gacctctata   2220

gcttttctcg aaatgaaacg tcttttgcct aagcatatct ttcttggagt tcagagacga   2280

tccccttctc ccgtttccac ctttttcttc taaaattgca gcttttgtta tagacagtat   2340

actctccccg ctaacccctg cagacttgct cttcgctact ggaagacgag ctgaacttct   2400

ctttgctgta atttccactt catgaagatg tgagcatata gaattagaca attgaacg     2458
```

```
<210> SEQ ID NO 5
<211> LENGTH: 301
<212> TYPE: DNA
<213> ORGANISM: Capsicum baccatum
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (186)..(186)
```

-continued

<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (301)..(301)
<223> OTHER INFORMATION: n is a, c, g, or t

<400> SEQUENCE: 5
gttcgtcaag cagagtctac ctaccatttt gttactttca gngtcagtgc anacgccatt 60
tgcagatttc tcattcatcg acatactcct tgacagagaa cttgagaatg gctcagaatt 120
tttgcgcacg aattgttttg ctgatgttgt agatttcaca tttccaccna atttccagac 180
tccagnccca cctgtctgct tccactcgcc gtaggcttta agtcccaaaa cacagttgac 240
aactctcgac gattttccac cctgataatt atatgaaaag aatgcagctt tatcagngaa 300 n 301

<210> SEQ ID NO 6
<211> LENGTH: 301
<212> TYPE: DNA
<213> ORGANISM: Capsicum baccatum
<220> FEATURE:
<221> NAME/KEY: misc_feature
<222> LOCATION: (187)..(187)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (275)..(275)
<223> OTHER INFORMATION: n is a, c, g, or t

<400> SEQUENCE: 6
aaatccagaa gttctgtcag tgtccgatca tgcctagttc aactcttacc ttgatgtctc 60
tttgctgttg gtcaataaat gtgttctgca tcatctgagt tcttttaagt tcctcattga 120
cgatgcgatt ctcttctttc actagtgcta aatttctttg gtcaacctaa ttgagaaaga 180
gaacaanaac anaaaaaggc actagtatga gtgaccctct atttacatga ataagtacct 240
tatgatttgc aaaaatcaga ggcattacct ttgcnctgac tgacgcatgt ttctgaagga 300
a 301

<210> SEQ ID NO 7
<211> LENGTH: 400
<212> TYPE: DNA
<213> ORGANISM: Capsicum baccatum

<400> SEQUENCE: 7
gcttgtggaa tcagttctga ataaggtcgt tgaggagttt gagcagcgca ttacaagcca 60
aatacaactg gtaagtttag cttctccgcc ttgttgcatt tgttttcatc tttcgtcttc 120
ttctctgaca ctgcattcac ataacattct atcagaacaa agcaactcca aaggactcaa 180
cagtttccag cggcaacaag ttccttcaga aacatgcgtc agtcagcgca aaggtaatgc 240
ctctgatttt tgcaaatcat aaggtactta ttcatgtaaa tagaggatca ctcatactag 300
tgcctttttt tgttcttgtt ctctttctca attaggttga ccaaagaaat ttagcactag 360
tgaaagaaga gaatcgcatc gtcaatgagg aacttaaaag 400

<210> SEQ ID NO 8
<211> LENGTH: 459
<212> TYPE: DNA
<213> ORGANISM: Capsicum baccatum
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (365)..(365)
<223> OTHER INFORMATION: n is a, c, g, or t
<220> FEATURE:
<221> NAME/KEY: misc_feature
<222> LOCATION: (374)..(374)
<223> OTHER INFORMATION: n is a, c, g, or t
<220> FEATURE:
<221> NAME/KEY: misc_feature
<222> LOCATION: (376)..(376)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t

<400> SEQUENCE: 8

```
cttttcttt ttagttactg gttgaactat ncgtgtgcga gtttttatc tgaactatca     60

ctaatttatc aaaatatgtc ttaattatta aggagtcgtt tagtagncgg ttaaagctat    120

gctggtatta ctaatgcatg gattggttgt gatttatgaa cgaatttatg tattatttta    180

tgtaggaatt agttatgcng atttttgtta tttacttaca tttttcatgt ataacgtatt    240

tngccttcta tcgtgnagga aatagtacat agatttgttt ataacttatg catatattag    300

ttagttatgt taattttta tttataaatc aaatattata tctatttata catgaataac    360

ttatntttta tccncnttgt ataantagtt taatagtaca taaataacat gtctcattct    420

caattaataa ttgtttaaat taggtgtgcc cttcaagat                           459
```

<210> SEQ ID NO 9
<211> LENGTH: 429
<212> TYPE: DNA
<213> ORGANISM: Capsicum baccatum

<400> SEQUENCE: 9

```
tgggggaatt ttgttaaaag gattctgggt cacataatct caagccatga tgtggatggt     60

ttgctgactc aaccagatgg tactagcata aacttgaaca tcaaggttgg tttagtccac    120

ctcaaaaagt taactcataa aatcttttta actaacacga gaagctcatt ttcttttctg    180

gctcttgaat tgcagaaggg ttctcaacac atgtgtgtag aatctcccgg agtgcatgaa    240

ctgagctttc caaattcatg tgtttcgttt gggagttcat ctgtggttat tgacacatct    300

aacctttctg tatgatcctt taggagttga attcttccat tctactattt catttatcat    360
```

gcatgtcttc tcatttattt tcttctgttt gtagcctatc tatttgaaag gcgagagcta 420
tctttttga 429

<210> SEQ ID NO 10
<211> LENGTH: 1348
<212> TYPE: DNA
<213> ORGANISM: Capsicum baccatum

<400> SEQUENCE: 10
caattctcta agcagatgat ataagttatt cattcctaac tcaagtatgt tgctcgatgg 60
atgagggtca acctgtattt atttttgaat tccgcagaat ctgctttccc tagaccatac 120
aacttaagaa gttgcgggga gggagggcta tgagagttgg ttccgtttta tggaattttt 180
gtaacctgtc cttctactgt attcttgtta actaaagagt gttgctcggt tctgctgcag 240
gcttttaatg gtggcgaatg ccggagactg tcgagcagtc ctttgccaca agggtgaagc 300
agttaatatg tctcaagacc atagaccgaa ttatgcatcg gagagaaggc gtgttgaaga 360
gttgggtgga tttattgacg atggttatct caatggtgtc ctatcagtga ctagggcctt 420
aggagactgg gacatgaagc tgcctcgtgg ctcttcctct cctctgatcg cggaacctga 480
attccgacag atcatcttga acgaggatga tgaattcctt atcataggtt gtgatgggat 540
ctgggatgtt atgtcaagtc aacaagctgt taatcttgta cgccgtggtc tgaagcggca 600
tgatgatcct gaacagtgtg ccaaggacat tgtcatggag gccttgcgtc tgaacacctt 660
cgacaatctt actgtggtaa tcgtttgctt tacttccctt gatcatcctg aaccatcaca 720
gtcgcgacaa aggcgattaa gatgctgcag cttctcagcc gaagctttgt gcagcttaca 780
gagttggttg gataacagtg gaaaccgttg agtttttcgt acatacaatt agttgccgga 840
gaggatgggc gcggtgtttg ttgtatggca gtctctcatt ttattagctg tacataacaa 900
ctactttcaa acttaaattc atcaattgaa atatttttgt caaagttgtt tgggtaacag 960
gctgaaatgt gtgggtacta actgtttctg tggttgtcga agctaccagt cgcatgaagc 1020
tatgaaatga gacaaccggg ctatagctac cgtaccacca gttagtcttc ttcctcctcc 1080
ggttcttggg aacttgaagg taagttcagt tttattggta taactaggtg tctgcagagc 1140
tcacgtcaat atttccatcg gatatatact catcatcatc ttgtcgattt caaaatttta 1200
ccttatctgc tacaagaagc gttaccaaac acttgatcat gacgaccaca acgttattgg 1260
tatgagtact gctgctaagt tgctggtgtg ggattcaacc agcgcggctc ttggctacgc 1320
gttttgtata tatcctttgt tgtcctct 1348

<210> SEQ ID NO 11
<211> LENGTH: 451
<212> TYPE: DNA
<213> ORGANISM: Capsicum baccatum
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (224)..(224)
<223> OTHER INFORMATION: n is a, c, g, or t
<220> FEATURE:
<221> NAME/KEY: misc_feature
<222> LOCATION: (272)..(272)
<223> OTHER INFORMATION: n is a, c, g, or t
<220> FEATURE:
<221> NAME/KEY: misc_feature
<222> LOCATION: (401)..(401)
<223> OTHER INFORMATION: n is a, c, g, or t -continued

<400> SEQUENCE: 11
ggtgactgac attgttgtcg agctttggtg gtatatgaac caactattgg aatccctcca 60
gaaactttgg tcatcaattt gaagaccttg ttagcttgta aaacggtttc tttgagtctc 120
aatgggttga gacagtatat tcaccaaatt atatttggtt tgaaacaaac ctcatagagt 180
tggtccatat ttncagatga atacttagaa ttgggccgat gttngagact atattgaaac 240
tttcctagct cttgaaggga ttgaaacact tnccgtgatc tcttgtgtga ggaaaagagt 300
gatgagtgtt cgcgcaattt gaatgtgttt tagccttatc ttcagcttgt tagctatctt 360
ttcaatctcc attgaagata gaaactcggt taactttgtc ntagaggaac agttgtgaat 420
atgctctcat aaagacaatt ttagatccat t 451

<210> SEQ ID NO 12
<211> LENGTH: 2160
<212> TYPE: DNA
<213> ORGANISM: Capsicum baccatum

<400> SEQUENCE: 12
gattgcattg atgcaagctg ttcacgagcc ccttgtgcct caagttttgc actcaaaagc 60
tcttggtaaa gctaaagcat taaaatataa gtcattgcac tgtagtactt acaggaaagg 120
tataatggat atcaaatgta aaggtcaaat gtaaaaatag atcctagtag tcaaagaata 180
ggcttgaaaa catgctcata acaatgcaga ataacaccaa tttctttggc ttatttgact 240
ggcaggatca tttgagtatg tatccaatag agacatgcta tacccactca actcgaaagc 300
tgtgaccaac ataatgtatt ttatgaatca cttacggagt aatgccttgt actgtatgga 360
atatggtaca aggaacagga catcacaggc aaactcaaca aacaaaacaa aaggccaaaa 420
cttgattctc actctgagat gtggcacgtg cagaggaaac agatgtgata agatgtgagg 480
taagaaagag gggaatgaga gacatatctg tgcctaaatt gtagaaggaa agcaaaatac 540
catttaaagc ttcatttaat aaatgaaact aataactatt gaataaataa aatcaccatc 600
agttacgtca ttctaattgt agtcactaca aaagtttttg agaatgtatc ttgggactaa 660
gtttaagaat atgatcttcg accaccaagg cttatatcct aggggtacca ctgtggatct 720
cctacacata aggtttggaa tcaaatcttt ctatcctctt ccccttcccc ttcccttgtc 780
cctctatgta acaaatgaaa ttaaaagaat gaaaaagtgt gactaaggca taacggaagc 840
ataggaatta attaatcaaa acaaatatgg atcttcaaat tcagattcag cattggcatg 900
ttttggcatt tgagctcttt aggtggcttc tcctcttcat tactagttag attttgaaag 960
cagtacttag taatgacatg cctacttcat ttataaactg gaaaattact aatcacgcaa 1020
cacttattac tatatctata aagaataccg catgtttcat atttcctggt gcattcatca 1080
tgcaagtggg agagaaacag aactttatta gtattctatc agttagaaat agcagatttt 1140
ctagtaacag ctctcactag ctgcttggtt gtgagaatac aatgataggg atagatatat 1200
acagtcacaa tatttatgct accattagag aaattctgaa gtgaccaagt gtatatcacc 1260
actttgtttg ctctcttgat ataaggagat aaattatcat aattgcaact ttcaatgcat 1320
aaaatgtgaa agactgatta cctcttcatg cttctctctt gcagatatgg tctgctcagt 1380
tgctatctca acaactgagt ccaaattctg ttggcttgag gatctctcca tttctaacat 1440
agtgacctgc acaaaagctc cacatttccg agaaacactt aaaaagcaga aaagtgacaa 1500
ggcaatcaat cttattcata tagatgccag gaaaatgaga aaagaaagaa atgaggacac 1560
cttctcttgg agctgcttaa tcaccaaaat agcttttgct tctctcaaag gtttgctccc 1620
acacaagtgc atcaaagagt tatcctcttg ctcagaacca tcgaccagat gaatgtcagc 1680
ctcaaaaagc ttccttgtga gatagtcaat ctttacctca ctcacggttt tctagcaaaa 1740
gcaaggatta aactaagaaa tcaaactgaa tcagaaataa cagaaggaag caaaagactg 1800
ttacatgtga ttcatatttt aaaagcaact cttcatacac cctttgaagt tccaggaaat 1860
cactgtcttc ctgccaaaat taaaaaataa taacacaaca gtggtataat acaattttga 1920
aagaaagctg aaatagcagc gcgaagtgtg aaccattgag aagctttttt tcctagaggc 1980
tccttttctc ctgctagtga catgcaacaa agcccgcggg tcagggagag tacagtcttc 2040
agcttgatta ctccttgcat tgtcttcttg cttgccagag tctaaattga tgtcaacatc 2100
taatagttct tcaaaaggaa gtaagggtcc aatgtcacgt tcaagccttt tggctttgac 2160

<210> SEQ ID NO 13
<211> LENGTH: 493
<212> TYPE: DNA
<213> ORGANISM: Capsicum baccatum

<400> SEQUENCE: 13
accgtgaggg atgcttttgt atatactgta aagccagtct taagtccaaa tatctgaagt 60
tggtttcgcg acttgctatg cttattgttt ccaagtaatt ttgttctgaa tggttgtttt 120
tagtgttgta atttgtaaat gatgatatgt atgttcttct acagaccgaa agttctggag 180
gttcaccaga gcaggatttt gtccagaagg catttgagat tcatgacaag tatatggtgt 240
atgtgaaagg ctgttttgct gataacacta tctttcacaa ggtattccga ctgttaactg 300
ctgtacgctg atccctttta cgatgaatta cttgagacgt tatatagtta tgttcagtgt 360
tgtcgaaggt gcacataaga cctgaatcga ggctcaaatg tgtttgagag tttagcgtcg 420
cttaatgtgc acatattcct ctgaatggtt ctcttaggct gatgtataaa ctctttgact 480
ctcataggct ctg 493

<210> SEQ ID NO 14
<211> LENGTH: 516
<212> TYPE: DNA
<213> ORGANISM: Capsicum baccatum

<400> SEQUENCE: 14
tgctattgag gatacattgg ataaggtatg cacaaatttt acatctccga tcaatttggt 60
ggtcgaactt catatctttg ctcaaacatc gtcaaaattg tgtacttttg ttaggtggtc 120
aagcttgtga tgtacatcag cgacaaagat gtgtttgctg agttctacag gttggaattc 180
agtgccagca gttgttttga catctttaac catttgatat gctaactgtc ttaatactta 240
taggaagaag ctttctcgcc gattgctttt tgatagaagt ggcaatgaag aacatgaaag 300
gcttatctta tcaaagctaa aacagcagtg tggtggacag tttacatcca agatggaggg 360
aatggtaagg attgttcaat ggacttagaa agttttgtct ctttaccgcg cttgagatat 420
ctgaaaacga atgactggaa atgtaaaaca ggtaacagat ttgtcattgg tgaaggaaaa 480
tcagactcac ttacaggaat atatcagtaa caaccc 516

<210> SEQ ID NO 15
<211> LENGTH: 1880
<212> TYPE: DNA
<213> ORGANISM: Capsicum baccatum

<400> SEQUENCE: 15

-continued gttccatgta tttctggaaa acagatggta caagggtggg tttaaggaaa gggtaatttg 60
gtaaacaaac attttttac aaaatttata taaatatata ttatctttaa tacatcaaac 120
caaacaatgt gtaaaaacaa atgtatgtgt aactaatact agcattacta ctacttgcat 180
taataataca agcattacaa ataccccta tttagcatta ttcttataca ctctaccaaa 240
cgacacccta agcactttgg catgtacaaa tactacctac catacgatct tttttaacac 300
aaaactttca tgcttgcaac agttttttgc atgtcgtctc aatgaatgaa ccaagttcaa 360
attaaaatgg gaactcactg gcagagtttt gcagtgctgc tatagattct ccttgactgg 420
ttccgttcac catgcttgga gctgtctaat tctagtaagg aggcaccatg gagaaacttt 480
aatgccgctt ggaaatagat acccgtactt tcacttgatc cagaactctg aaccaaatag 540
ccaaagtcaa cataaaataa ataaatgaaa caaataagaa agcatatcca ccatattttg 600
tcccctcctt tcttaggaca taagtgtaaa ttcttttaac cttgagacga tctgccagat 660
gttttaggtt tgtggcttct tttatggcat ttgtagcagc ttgacttgat gaatccttct 720
gagcagggct gggaacatct tgatccctga ccttattagc agtattatta ggtaggtttc 780
catggtggct tttagctgtt ttaccctgtc ttgaagcatt tgacttttcc ctttcagaag 840
catcaactat aacacaattt gcctcgtttg cccgtccgga tccaggaact ggctctttaa 900
atacaaccgt ctcattctga actcttgtta atggaaactt ggaagagact tcaatctgct 960
cacttctgtt ggaaacaagc ttcttagatg atctctgatc atttcgatct ggtagtgcag 1020
cctggctttt atccaggcgg gatgcaacat ccgatcgagc ttctgcacca tcatgatgac 1080
caactcgtgg ttgattatca cctttaacat ttttgtccaa taattttcca gatgaatcct 1140
tcttagaact cttctttaat ctatctgaac caacaacatt ctcctgaaac ttgtttttc 1200 ctggtgccgt cttctcctcg tctaatggca tttgatctga agataaattt aaaatatcag 1260
gatttttggt gttacattgg tcagaatcag attctggagc ccgattcttc tctttgcgcc 1320
gtgacaaaga acctctttta ccatttgaga caaactcact atcctgacac tgatagtcat 1380
tctttctctc cttatcagag ccttggtctg agttttctgt cttgcaagaa aattgaccaa 1440
cttgacgtaa tggatcggca tttacatcag catccagatg agttgcataa ccagagacca 1500
tggtctttgc tttaactgtt gtatctgatt cacgatggac atctttctcc tctaaatcag 1560
cttcagctaa cacaacataa ctcgtgccat tgcatgcact atccttctta acaaaactgg 1620
attcatttga gaacccatca ttttcaccat cagaagacct cttgggactt gaagtgggaa 1680
cagctgatga ggcagcagca gaaggccgtg aattgcctag atcctttttg aagaatctgc 1740
agcttttaca ctctgcaaag atacagtgag atcttgccca gcctgctgtt ccttttttaac 1800 tcgacatgtt ccagcactac ctttgcttgc gctagtgtct ttccggtcag acttggagac 1860
ccttgctttc ttttccttcc 1880

<210> SEQ ID NO 16
<211> LENGTH: 2286
<212> TYPE: DNA
<213> ORGANISM: Capsicum baccatum

<400> SEQUENCE: 16
gttaggggaa gtacaaataa atcagcaagg aaaagacaag tccatttcat attgcagaaa 60
acatgttttc cacttcataa gtaggccatc atagatctat aagggattat tgatcattct 120
agtgatagtg ttcttaaccg ttactaacaa agatgaagga tatgtatagt tcttggtgtt 180

-continued

```
agtatgccca tgagaattgt aagatgggat tttagtttca ctataagctg catttttgtt    240
tcacctgtaa catcttctgc tatctagatt ggacattgtt ttggtctaca gctgatgaac    300
tttgagcagt ggactacgct tgaaatttta aaattatcca ctatgctgat ttttacgcat    360
taccataact aactgcattg cggtgaaaac tcaatgcatg tccttaagcc gtaggttgct    420
ttctaatcag caaacaagtt tggtgaacaa gttctctgaa tctatccatt ggttatcctt    480
gtctcgacaa gctagttctt tttccttttc tattctgttt gaattatatg agtcagcaaa    540
gtatagattt tgaaggagtt caagtaggaa atattaccgc tttggaaatt tacagatttg    600
cttttaaaac tttaattatg tgccacaagt ctagcttttg gaaatattta acatgcttct    660
tgaactgggt ttcataatgg tcaagtgccc atgaatttta tttttctct tccgctgaat    720
acattatcaa acttcgaact tgaatcttca ttactttgca gacaactaga gtatttgctc    780
cttggctcaa taatgcaagc ttagagaatg aagaatcttg gcatgaaatt gctcgccctc    840
aagttcatgg tcatgacata aattgtgtga cagtaatcaa aggaaaagga aaccatcgtt    900
ttgttggcgg ggctgacgag aaagttgcca gagtttttga atctcctcta tcctttctga    960
agacattgag ccatgttact tcagacagct ctagtttttc tgccgacatt caagctgatg   1020
tgcagatatt aggggcaaat atgtctgctc taggtctatc gcagaaacct atatatgttc   1080
agggtgagtt ttccagtcta ttgtgtggta tcaattttgc ataataacat ataagatact   1140
cctattcatt tatgtttcca tcatcacttt tgatgttaca gggtgatata taactgagtt   1200
gttgacttgt caaaattaac tgtaaagacc ttctcttaac catgtattga attagaatta   1260
atgtgatgtg ttaccgactc tttctctaag tttgcttaaa gtgctgtgat atctgatgca   1320
aagtgttctg actttgatac aaacagcgat tatcctgaat atttcgtttg aggactctta   1380
tatgttataa tatctcatac atctaagcct atcttttgca gcagcatcga caccaacaga   1440
cagaagcaat acggaaggtt ttgatacact agaaactgtt cctgaagcag ttccagttgt   1500
cttgacagag ccacctattg aagagcagtt ggcatggcat actctatggc ccgagtcgca   1560
caaactttac ggtcatggga atgagatttt tgctctatgt tgtgatcagg agggaaagct   1620
tgtagcttca tcctgcaagg tttttctctc tttccctttt ctcctccttt cttttgggtg   1680
ttggcatggt tcttccttgt ctgtcttgaa tcttctgtta atagcattca acttgattgt   1740
acttttgcta agtgccctga taaagttggt ttttagtttc tggtcttaat atacttcgat   1800
agaaaaaaaa ggtagtactc cattccatat atggtgtcaa tttttttcaa tatcttgacc   1860
attagacgcc cctattttat tggtggatgg ggttagttaa ggaatagctg ggtttgatcc   1920
tgcggcattt tctctcttat gagaaatcaa acgccaatct gctcatttta tataacttac   1980
tggtgatgct cactacctcg gacttttacg ttgttagaga cctctatgaa ctatagcaac   2040
acatgatgga attcacaata ttcttctaga tactcctttc aacttctaat gatttttttg   2100
ggggaagtct ttattttctt aattagttgt gtctatcaga aacactctct ctacctccga   2160
ggtaggggtg acgtgtgcgt gcgtacactc tacccttcct agacctcact ttgtgtgatt   2220
acactggaga tgtttttctg ttcttattta attgtgaata ctaattatgc tggggctata   2280
taatcc                                                              2286
```

<210> SEQ ID NO 17
<211> LENGTH: 358
<212> TYPE: DNA
<213> ORGANISM: Capsicum baccatum

<400> SEQUENCE: 17

```
gattccgtaa tcactctaac ggctgaaata tatctgattt agtgcttttc ggttcattat     60

aatcagtaat ccagccagta tgggtgacgg tcatgtcaat aatctgaaat gttatctgcc    120

tttttctgta atactatagt ctatagtatc atttatgtgc accaagagag cgaactaagc    180

atcaatccac gcagctattt ctgtttaaga atttaggcta agtagatttt tgtgccagta    240

aatgttttac tcttttagtt tctaagttga aggtgattca ttaattactc ttttagtttt    300

taggttggag gtaacctcta tgcagattta gttgggttta taaggatgca attatatg      358


<210> SEQ ID NO 18
<211> LENGTH: 1273
<212> TYPE: DNA
<213> ORGANISM: Capsicum baccatum
<220> FEATURE:
<221> NAME/KEY: misc_feature
<222> LOCATION: (470)..(470)
<223> OTHER INFORMATION: n is a, c, g, or t

<400> SEQUENCE: 18

tgggggcatc tctatggccc gagtcgcaca aactttacgg tcatgggaat gagatttttg     60

ctctatgttg tgatcaggag ggaaagcttg tagcttcatc ctgcaaggtt tttctctctt    120

tcccttttct cctcctttct tttgggtgtt ggcatggttc ttccttgtct gtcttgaatc    180

ttctgttaat agcattcaac ttgattgtac ttttgctaag tgccctgata aagttggttt    240

ttagtttctg gtcttaatat acttcgatag aaaaaaaagg tagtactcca ttccatatat    300

ggtgtcaatt tttttcaata tcttgaccat tagacgcccc tattttattg gtggatgggg    360

ttagttaagg aatagctggg tttgatcctg cggcattttc tctcttatga gaaatcaaac    420

gccaatctgc tcattttata taacttactg gtgatgctca ctacctcggn acttttacgt    480

tgttagagac ctctatgaac tatagcaaca catgatggaa ttcacaatat tcttctagat    540

actcctttca acttctaatg atttttttgg gggaagtctt tattttctta attagttgtg    600

tctatcaaaa acactctctc tacctccgag gtaggggtga cgtgtgcgtg cgtacactct    660

acccttccaa aacctcattt tgtgtgatta acactgggga tgtttttttct gtttctattt    720

aattgtgaat actaattatg ctggggctat tatatcctgc aggtcaatca ccaccattgt    780

tgaaatatgt tatgggcagt tgggttctgg aaaatcattt ggtcttttgg cattccaaat    840

ttaaaagtga ccccaaggga tttccccatg aaaccaattt ctcttggcct ttaaaaaaac    900

cccttttttg ttttttaaat taatcaaaag gtttgaacat ttaccaccct cctttgccaa    960

aaattttaaa aaatacaaaa ccaaaaattt tttttccccc accccaatgt ttatatatac   1020

tgttaatata aaacttttct cccttttgga agttttttttt agaaaaacct ttctactttg   1080

gagagggaag agcctggcca actccccccc aaaaccccca cggtgtaaaa ttttattttc   1140

tttcctcccc cccctccacc ccccctcctc taccaccccc ctaaaataat ctccctttttt   1200

ttaatataaa aaacaaaaaa aaaaaaccct cctcttttta acccccttccc cttaaatttt   1260

ttatttcccg cca                                                      1273


<210> SEQ ID NO 19
<211> LENGTH: 1253
<212> TYPE: DNA
<213> ORGANISM: Capsicum baccatum

<400> SEQUENCE: 19

gcagaaatta aaatacacag gtaagataag tgggaagcaa catctaattg ggattttttct     60
```

```
tttcctttca tatttacaga ttgttttgta tttagacaaa ggagaaaaaa atctaaaaat    120
aacagatagt ggcggagcca cctttgctcc aggggttcat ctgaatccct cgatggaaaa    180
ttttaccgtt tttataatat ttttacatgg ttaaaaatat ttttattcat gtatagtaga    240
tgttgaaccc cgttcgacta gttcgtattt atacttccgt accccctcaa tgaaaaattt    300
ggctccgaca ctgataacag aatgtgatat agacaaacaa caccgtcaga ttttcctcta    360
tttataatgg acttgttgtt atttactgtg caatcaaact aacctttcct ggttagctct    420
tttcatgaaa cttatccaca tgcaagacta cagtacttga aacagataaa agtggtacac    480
ttgtcttagc agatcaacta atgttgcact ctggatacga ctccagtggc gggcttgtta    540
aaacctgcag gaataacatg tgaaatttca aaactttcaa gcattcaaca aatatcatct    600
caagtgttga aattccaaag tatatgtcct gaatcttgct ctaatatcca agaaatttaa    660
ataataaaaa aaaaactacc ctaggacgat atatgtagtc tgccgatatg atcttcttta    720
gagcagtctt ccaaggatgt gataggggat tgaaaatggg aacatagaag aattgatgaa    780
aaaatttcca agagttcaaa ttatttctac tggtgaggct gttcatagtt cagataagaa    840
gtgtaccaac aatgcaagtt gcagcaatat ctttgctgtg cctgcactca atattgagac    900
atccttcttt cgaatacatc tacgcattca caatgaaccg ataaataaaa gatttgttaa    960
atactgatca ttttcagatc aagattatcg aaagatcact tgaatggttg ttaattttaa   1020
aatggtaaca aaagggagat agcaagtcca tttcatgaaa ctccacaatt acagcgtatt   1080
tgacattgaa aaggcaacat atatgcaatt aaaaaaaaaa agaaatgagt ctacatcttt   1140
tcaaatacaa aagaaaatca aactcaccat ataaagtcta ccaaaagaaa gtgacatagc   1200
accgaagata tatggactcc ataccaccct ttactctgat aaagaagcag tcc          1253
```

<210> SEQ ID NO 20
<211> LENGTH: 1323
<212> TYPE: DNA
<213> ORGANISM: Capsicum baccatum

<400> SEQUENCE: 20

```
ctaaaatttt agcgtatttt tgtcaacctt tttaactgac atagcacctt tttagctaac     60
gtggcacctt tgacgtggcc cccattttta tgtaataaag gtgccacgtc agcacaaaag    120
agtgacaaaa atacgctaaa attgagttcg gggataaata ggaccccgtg aagttggagt    180
gtgtcatagc aactttggtc ataatacaag ggggtacaag atgcttatct cgaagaaaaa    240
tgaaaaatca caagcgcaac gtactttata tgtcagagtg tagcgagtgc acttcaagat    300
gtataataat ttgctcgagg atacagtact aattgaagcg aattacatcg tttcccctat    360
ctatttaata taagaaaggt tttgccgaag aattgggtga aggtgattag acatgacatg    420
acacaacttc aactgaccga ggacatgatc ctatatatga aggcatggag gtcgaggatt    480
agcgtcgaac gttaataggt agacacaagt tgtcatactt ctagtaggat gatttaggta    540
tcacgtagtt tttcccgcct atgttcatta ataactgttg ctatacttgt tttgtgtatt    600
gtttttctgt agtctctctt ttttctctta cttccttgct tttttgcgcc gagggtctat    660
cggaaacaac ctctctaccc cacaaagata gaggtaaggt ctgtttacac tcgatttact    720
gagctcggtc gaggttaagc tgatagctca gaacttgaat gtatattcgt tggtcataat    780
caatctccga accagatcaa cagctccgac accaaggtag ttgagttaag actagcacaa    840
ctttaactaa gctcgcaact tctagtaaag gacgcgtggt tgtgaaacat ggcctgtagg    900
ttctttgttt ttctttgaat aaccgagaaa tatgttgttt ttatcttcaa aactcggtgg    960
```

atgtttaagc cccttttctc tatctttctc cgtttaaata ccaaacttaa ttcaccgata 1020
gaatttgagc tcatgatgtg cgcctactac acattcttct tctaacaagc atgcgagtga 1080
caggaaaggg cagtaaggaa acaaagaaga tcatatcaaa agaaaatgtg ggcgaacctg 1140
gttgattcct cggtcctttt tccagcaatt ttgcccttgg gagccgctga caactgtaaa 1200
gattagaaca cgggatcttc aactcctctc ctccttgtaa gtaagaagac tagttgtttc 1260
actgtaacta ataatgaaac actaacctgt gaggcaatat cgattccaat ttcatcgagg 1320
acc 1323

<210> SEQ ID NO 21
<211> LENGTH: 786
<212> TYPE: DNA
<213> ORGANISM: Capsicum baccatum

<400> SEQUENCE: 21
actccatttg aactcatctc gttccaatgt tatgtcaata cagataaaag cttccacctt 60
gagtaggggc aattttctga aacatatccc ccgctacaaa gtccaaattt tcacttcctt 120
gcagattagc cacgacaggc ggaagatcaa gaacaataca tttcatgtca gggaattttt 180
ttgttatggc cattgcaaca gtaccatttc tcctccaaca tccactaaag atgtcaatcc 240
tctgaaaaca tccttaaact cgttgccaat cagtacgtta atgaatgatt gcgaatctct 300
agccatgttc gcgtgaaacc agttaccact actcgtatct ctcgaaagtt tactccagaa 360
taaatctcca tatgctgtgt aaaatgcatt tggatcctca tttctgaacc aatcacctaa 420
acagttcgat ccatgcttta aagaaaaatg aatcttgatc ttccatcaag ttccaaggcc 480
catccttcat tatatatcgg tcagctagtg caaccgaata ataccccttta ccatcatcac 540 catcgtccac attgttgtct tcatgttttt gtagaatcaa caagccataa cgaactacta 600
ttggtgtaag gcggtgaaag tcgggattat ttgaagggct aatagacagg gaagacatga 660
gttttgatag tgtcattggt tttccttgtt tggttaagtc attaggtatg cctaattgaa 720
gtgcacattt caatgttatg gtaaaagata tgatgaattc aacaaacgtt gacacttatt 780
attttc 786

<210> SEQ ID NO 22
<211> LENGTH: 597
<212> TYPE: DNA
<213> ORGANISM: Capsicum baccatum

<400> SEQUENCE: 22
ggcaaattgg tacttctatc catggaaact attgcagatg ttccataacc aggtagatgt 60
gaagtagatg tttgagaagc aagtgagaag tgtgaactcc tctctcgaac agagggagaa 120
gtgtgtcgtt tatgaatact accatcttcc tcatttatga tctgcacaaa tcacaatagt 180
tccacacttt actccacaac atcggcctta aagactattt cggaaaagat gcccattatc 240
tgtcttggaa ggatgctggc agtaatttat aagagaaaag agagtaccct ttggatagca 300
ggatccaagg acgaaagcaa acgcctagaa cgttctggcc aagttcttgc aaacattctg 360
tacaaaattc ttgcagttga tcggacctgt tgttaaatcc aagggatatg aattgccaac 420
agatcttgaa tcgaattaaa gggggtatac atgcagataa ctatgccaaa atatgatact 480
cagagttcaa caagcatacc tcacccattg catcagagac acaacacttt ataaggtctt 540
catagagctc tgctgaacgt tgtacctcag atgcatcagg ccaatgttca aggatca 597

<210> SEQ ID NO 23
<211> LENGTH: 1085
<212> TYPE: DNA
<213> ORGANISM: Capsicum baccatum

<400> SEQUENCE: 23
ggatccacga acctaataag caccctccat ggatacctcc acaaccgctt cctcccatcc 60
acgcaacaac atgcctagtt caatcgcaca aaaggggtct agggagagta gagtatacgc 120
agaccttacc cctaccttgt agagataacc aaaaccctaa aacaatggat caaaactcct 180
gtttcatata gcctctaaaa ccccgcttag cccagtttct gcccctctga cctctggtcc 240
actgggacct tgcctaccca tatagccact tgccaatgga aaactggcta ctcagatgga 300
tgcaagacca atttgataat ggaaacctca tagcacgaaa ggcaaagttg ttggttatcc 360
taaaaataaa agcgattata ctcaaacgaa aaatgtcatg actgatatct tcataaaaat 420
cttggttcat ttacacattc atagtatact tacaacgaaa gtaataaaaa caaaggtaat 480
atactacctc aacagaaatg ggttgagtt tgagacagtc gaaactacaa tgaattttca 540
ccttcttgct ttcttttata gatttcttaa ctttttaaat gaagatgcac tagatacttg 600
tactaaatag tccaatagca agatgtatca ggagggactt tggtagcaga tctaatctag 660
ctgaggatgc tacattatcg aagttgcaag aggcgctaat acaataacaa cgacacacgt 720
atagcaaatc tggtttctcc gaaagagagg aggagccttg aaacaacgat aaagttgtct 780
ccatggttca agccgtggaa ttaaccgctg atgcttgtta gagtaggctg cctacattac 840
acccctcagt ttgcgaccct actcggacta tgcgtgaatg caggaagctt catgcaccga 900
actagctttt ttagttctcc ataaacccat acgtcaaaga gaaggcttgt tgagtatcaa 960
agttatcacc acaaatgcaa atggcaattg aatgcaatgc accatcacca gcaaaagaat 1020
agacaagcga caaccaaata cggcagcata aaacaccaag gcaataaact tcaatctaca 1080
gttgc 1085

<210> SEQ ID NO 24
<211> LENGTH: 756
<212> TYPE: DNA
<213> ORGANISM: Capsicum baccatum
<220> FEATURE:
<221> NAME/KEY: misc_feature
<222> LOCATION: (756)..(756)
<223> OTHER INFORMATION: n is a, c, g, or t

<400> SEQUENCE: 24
gatgatgtcc acaggatgca gcatggtccc tatgatgtat cctggattcc cgcaatatat 60
gccaacaatg ggaatgaaca tggggatggg gatgagtatg gaaatgggca tgaatcggcc 120
aatagttcct tatcagccgt taatgccaag tccagcaatg cagaatgcag ctgcagtagc 180
acaaatggct cctagatatc ctcttccggc atatcatttg ccaccatttc ttgcacctga 240
ttcatccaga atccctgttg cgaatcagcc agatcctccg aggctaaact cacttgttgg 300
acataatacc aatcagccaa aacttccgca ttttgctgat tcatatgatc aatattttgg 360
tctccagcag gcacgactga tgttacccca ggcaagtcct tgttcttctc acacactata 420
tttatttatg tccttcaccc attgatattg caccttaacc tcattactgt tcacacccac 480
ctaattgtga gatactgatg aaactcacta acctgactaa tccaaattaa cgcatattta 540
tattatcgtc atgataacta cgttcatgta gaaattatca tctagaatat catcttgcaa 600
cataaactaa actctaaact gtggtcagct gcctacaaca gcttgtttca tcacctcaat 660

```
ttattgcacg ttcttccaag aaatcttttg acaattcatt gtattgaaat acaggataag    720

ggagtggaac agctgaactg cagtaaaccg aacagn                              756


<210> SEQ ID NO 25
<211> LENGTH: 481
<212> TYPE: DNA
<213> ORGANISM: Capsicum baccatum

<400> SEQUENCE: 25

ggtgtcaaag aggcacctct ttgtccattt gttgtatccc ccgacacaac atgagtagaa     60

gttacttcct gatctccgtt ctcaccttgt ggtgcagcat ttagatccac atttagcacg    120

gtatttcttc tcgagttgga ccttgtacgc ttattttgtt gtgcccttct atctcgggta    180

ctcatgttat gctcagttgt accctaatta aaacaggaaa agacggaaaa atttgaagtc    240

atgatagggt ttatattctt aataatctat tacctcaaaa agcaagaata aaaagaagta    300

gtagtaatgc aagtatctca aatttactaa atatacttcc gcatgagcta ttacagtgga    360

ccttaacata caccacggcg atcaatgaat agacttgcaa attgtatgtt ttcaagaatt    420

ttagcaagtt gtatttacat tgggctgcga tctggaaagc aaagcatgga catcggaagt    480

g                                                                    481


<210> SEQ ID NO 26
<211> LENGTH: 554
<212> TYPE: DNA
<213> ORGANISM: Capsicum baccatum
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (217)..(217)
<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t

<400> SEQUENCE: 26

ggtgttttat gctgccgtat ttggttgtcg cttgtctatt cttttgctgg tgatggtgca     60

ttgcattcaa ttgccatttg catttgtggt gataactttg atactcaaca agccttctct    120

ttgacgtatg ggtttatgga gaactaaaaa aagntagttc ggtgcatgaa gcttcctgca    180

ttcacgcata gtccnagtag ggtcgcaaac tgagggntgt aatgtaggca gcctactcta    240

acaagcatca gcggttaatt ccacggcttg aaccatggag acaactatat cgttgtttca    300

aggctcctcc tctctttcgg agaaaccaga tttgctatac gtgtgtcgtt gttattgtat    360

tagcgcctct tgcaacttcg ataatgtagc atcctcagct agattagatc tgctaccaaa    420

gtccctcctg atacatcttg ctattggact atttagtaca agtatctant gcatcttcat    480

ttaaaaagtt aagaaatcta taaaagaaag caagaaggtg aaaattcatt gtagtttcga    540

ctgtctcaaa ctca                                                      554


<210> SEQ ID NO 27
<211> LENGTH: 301
<212> TYPE: DNA
```

<213> ORGANISM: Capsicum baccatum
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (251)..(251)
<223> OTHER INFORMATION: n is a, c, g, or t

<400> SEQUENCE: 27
agatattaag gaggtgaata aataaanaat cngcccatgt naatgcttat ctcaacagca 60
ccaactaatc atgaagtatt cacacaaagc atntcctgtt ccgttgtcaa gaatcctcaa 120
ggcctccatt gtttattntc acaatctgtt gtcaaagttg atgccacaag gccatnatta 180
gaagtattga atctncagca attatccaaa caaaaccagg agcgtcgaac ctccttnctg 240
acactgtcct ntatatgtaa agtttctcaa cggggcaact ttctggtctc atttctggat 300
t 301

<210> SEQ ID NO 28
<211> LENGTH: 1216
<212> TYPE: DNA
<213> ORGANISM: Capsicum baccatum

<400> SEQUENCE: 28
gacaaagacc acaagaaagc tctactcatc ttatcttttg ctcttcttgc aatccttttc 60
catcatcctt gtatattctg attcaccatt ttgatcttca atcaattcat aataacatcc 120
aggcactcct tagagaattc acggagaaaa tatcgatggt atagagtttc agattgagta 180
ccacataata gggagccatc atcatcacta agtccaatat gcttcattct tgccttggtc 240
atgagtcgtt tatgcatggt tatctaacat ataaagctat gcgttggtat attggattta 300
ttccacactc ccctccattc aggccagcaa gagccaatcc ctatttacag atatagccac 360
tcagaatagt atattgtcat tccctttaag ccatccattg tgaacatgcc ctgccacaaa 420
tttagccttt agtccacaaa ttttcttcca gtggcaacat gaataagtag gggcatttaa 480
actttaccaa gacaaaaata gaagtcaatc ctcaacccca gatagctatg gtatagatgt 540
ctacctcaag tagctatggt ttctttctat caacagtgac aaaattaaaa tatacatctc 600

```
gtaatagagt tactttttag taaggtatat attacaaaaa gtggaagaag tcacgtaaca    660

aactatgatc agttagtgtg ctcaatcgta tactgttgta ccgactagct ctgatacaag    720

gctttttgt gtcactaatc tagatgcact agaaatacaa taggcagctc ctatcatcat    780

atccagcagc attaggcacc gaagtgccaa acccattgga gacgacaata actatcggca    840

tgaaacattc atggagaacc ctctttttct caatagttct ccccacgtct ctctctctct    900

ctctctttgg tgtgtatgta ataggtactc ttggaaaaag acaagttaac tctaagagaa    960

aggagtcatt caaaacttca aaccagaact tgcagcacac ggggctctcc tattatcctc   1020

agttaaagaa tgggtatcat caatctcaag tataaaatgc tcagcacata cgacatgtca   1080

agtatctttg ttttggtcga cctgaacact atattattaa actccctagg gaaagagcca   1140

atcttttgta caactcaaag cagcaagtaa aaaataagta atctacacct atcgactatc   1200

cttctagcta ttcctc                                                   1216
```

<210> SEQ ID NO 29
<211> LENGTH: 893
<212> TYPE: DNA
<213> ORGANISM: Capsicum baccatum

<400> SEQUENCE: 29

```
gaactcctct tgtgattaaa tcttctagcc atgatctgtc tttacacgtt ggctccttca     60

tgagctctct agtatgcaag catttgtttc cattttaatt ctttggttca ctatctgtgg    120

gcatgggaca ttgtgattca atagggcctc attctttgcc atccaaatgt ggtatattag    180

cgctgcggct tctgctcata tggttccct gctaacccat ccatttgttc gtctcactat    240

cctagttcag aacccctcga tggttttatt ttttatcctt atttttagca attggaggtt    300

ctcttctaag ctagcttttg aaaaaccgct ctcgaaagat aaagatcatt agtttcattc    360

tcccttccac atagtaggca gacttcgtct tggcatatcc ccattcagta taatcgatct    420

cttgttaata gtctcccctg tgcatagtta aacaacaaat gaggctgtgc tttggaacat    480

ttactctatt ccatacacct ctccaagtgg tccataggcc tccttctccc tttgtccaag    540

tgcagcaact tctgattgtg tatttgcctg aacttgtgag ccagccattg tgtacatagc    600

ctggagcaaa cactgttttc actctgcaaa tcattttcca gtaccagcag atattaatgg    660

agggtctata ttcccaccag ttgtcaccct ttaagtaaag tggttcaccc atgtaaccca    720

aaggttatca gcttttcttg ctttgttcca tacttatttc gctactgctg cttcattcca    780

agatacagtc tctcacccct aaacttccgt ctttctttgt tctacaaatc atatcccaat    840

atatatagga ggtagttagc ctgtgttaac atttccactc catataaagt tcc           893
```

<210> SEQ ID NO 30
<211> LENGTH: 301
<212> TYPE: DNA
<213> ORGANISM: Capsicum baccatum
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 30

```
ccataatctg gtttgttgct gcaccaccaa aactgaagtn tcactttcaa aatctgaggc     60
```

```
nacaagaatg cctcctacaa tacctaattc accatcctca tcagtcctct ttgtcaattg    120

caacaatatt ggtgagtcta cgtgacgttt accaaccata acaagatcat aaaaacgtcc    180

caaagattta ataacttcta acacgtccgc gcctcttttc acctctgctt cttgataaga    240

aacttgttct gaatgaaggt attggagatt gaattcattc aagatttgtg aatcaagaac    300

c                                                                    301


<210> SEQ ID NO 31
<211> LENGTH: 301
<212> TYPE: DNA
<213> ORGANISM: Capsicum baccatum
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (241)..(241)
<223> OTHER INFORMATION: n is a, c, g, or t

<400> SEQUENCE: 31

atttttgatg agtcagagcg acatangtct atacaactat aattagttta tccttctcaa     60

atgtgtagac tcttcaggat catgaagtcc ccataatctg gtttgttgct gcaccaccaa    120

aactgaagtn tcactttcaa aatctgaggc gacaagaatg cctcctacaa tacctaattc    180

accatcctca tcagtcctct ttgtcaattg caacaatatt ggtgagtcta cgtgacgttt    240

nccaaccata acaagatcat aaaaacgtcc caaagattta ataacttcta acacgtccgc    300

g                                                                    301


<210> SEQ ID NO 32
<211> LENGTH: 301
<212> TYPE: DNA
<213> ORGANISM: Capsicum baccatum

<400> SEQUENCE: 32

gttcaaaaac acgaacttct tagccataaa tcaggaatct tataggtcat gcgtttgaag     60

acttgctctt tgttattttg agtcgtctac cttttctagc ctctggtgtg tcttttgata    120

aaattattgt gaagtcctcc cgaaaaaaaa attgtgaact atcgagcttc actcccttga    180

ccggagtgtt atcttggttg aaatggataa tccatcagat gacttctctg gatatatcat    240

tcagcttccc gacgattgtc tactctgtat ttttcaactc cttgactgtg gatctgaccg    300

t                                                                    301


<210> SEQ ID NO 33
<211> LENGTH: 733
<212> TYPE: DNA
<213> ORGANISM: Capsicum baccatum

<400> SEQUENCE: 33

gcaagagtta tcacttaaag gaaagaactt gataggcaga aagccaagtt tcacaagcta     60

gattttctgc actaactctg attttgaaat cttgtactac ttttaagtat cgattacaag    120

cacgacatgt tcattagctt cctacttgtt tatcgtaatt atcaaaactt gatttagatg    180

gagtcttggg acagacttta ttgtgataaa aagttgcaga ctttttgtga gagatgtagt    240

tacaacgata gctactgatt gactcgtgaa aaataattga actggatgct ccaatgggac    300
```

gacctagcca atgatcgagt tggagtatag accttggaac caagattcta attccagtag 360
aggtgataca aagtgaaatt ttcccatcta cctgggcata gttagctgat atcttttctg 420
gtgggaggta acaagtacac ttaagttagt tgaggagtgc gtgaccttcc cgctagctca 480
ggagtgtgca agcttccacg aataccatga tatctttaaa aggaggagtt gatatggtta 540
caggctcttc caagtcttgc ttcttataca ttttgtacgt gcaaacaagt tgctgaaggg 600
tagatttgat tacaaaaaag ctatttacga caaagatatt gctgtcatgt acttgtacat 660
tgtatttctc tttgttttat tattctttgc tagccgaaca aatttgcttt actctgtgat 720
ttgcagtggt gat 733

<210> SEQ ID NO 34
<211> LENGTH: 430
<212> TYPE: DNA
<213> ORGANISM: Capsicum baccatum
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t

<400> SEQUENCE: 34
tttattaaca cattttgtga ctttaacaga gaagatcant tcagnatctc cagtagaagc 60
aaaaggaaaa taggagaaga ttcaaagaaa tcaaagaaat gatttttta aaaacacctt 120 ttttttcttt ggtcctaaaa agtctacaaa ttatctagtt ccttggtttc ttcttgaatc 180
caaattgttt gagttcccac aacaaatttt actaggttta aatttgtcac agttgtacta 240
tactataatg tgttcgtcaa tatcttatga tggtgtatca atactgtgat ttgcatttcc 300
aggtacatat tatgttatcg tctgggtttc tttatcaata ctgggattac acttggtatg 360
ttgttgttgt tgttgtagta agcgtttagc ctaattaagc tgttacccaa atttcacgtc 420
ccttatggct 430

<210> SEQ ID NO 35
<211> LENGTH: 1887
<212> TYPE: DNA
<213> ORGANISM: Capsicum baccatum

<400> SEQUENCE: 35
tatagtgcag caggaatact tttgaatcag agaaagtatg tgttggaact tatatctaag 60
ttaggtttga gtgggtcaaa acctgctccc acacctttgg aacttaatca caagctcacc 120
acaatggagt atgatgagat tacagataat actgctggag atgaactatt gagtgatgta 180
agttcatatc aaaagttgat tggaaagttg ttgtatgtta ccatcacaag gcctgatatc 240
agcttctcag tgcaaaccct gagtcagttc atgcagcaac ccaagaaatc acattgggaa 300
gctgcactca gaactgtaag atacctgaaa aatgcaccag gtcaaggaat ccttatgaaa 360
tctggtcata ctcaacaact tacatgttgg tgtgactctg actgggcagc atgtccaaac 420
accagaaagt cggttactgg ttttgcagtg aaatttggag agtccttgat ttcttggaat 480
caaagaagca acaaactgtc ttaaggagct cagagtatag aagccttgca gcagcagtag 540
cagagttgac atggttgcaa ggattatttc aggagctgga tgttcacatt gacaaaccta 600
ttgcagtctt cagtgatagt aaatctgcca gattgcagag aatcccatat ttcacgaaag 660

-continued

```
aacaaagcac atcgagatcg attgccattt tatcagagac gagattaaag aaggagtggt    720

taaggctgtc tatgtgaata cgaaggaaca agaagctgac ttgctgacta aggccttgac    780

tacttctcaa cacatgcatt tacttggcaa gcttggagtg ttcaacattt tggaccctcc    840

agcttgaggg ggagtattaa agtcaattag agtcagttag ataggtgctt agctgaagtt    900

agttgcggtt gttagtggta gttgaagttt gttagtagtg gaagttgtta gccagctgtc    960

atgtccagct gtcaatgatt aagttagtgg ggcaacaatg agggaagtta ctagaagctt   1020

atgagcttgt gtatatatat tctattccag attgaataat caattaattt cattaccaca   1080

aaatatcttc tttctcaatt cctatcataa actagcaatt ctgtcacttg atgttgcttc   1140

agttttgggt atgggattca ctggatactg gtgttttcga tttgaaatca tctattccat   1200

aatgatgact catagactga tagtacagtc tattggcccc tgttagagtt tatgacccgg   1260

attttgttga tccggccctg aaaagttcac ggtgcgatcc atgtttgtgc tttttgtggg   1320

gtctgtggtg gtgatgtttg tgagcttagg atttatttgt atgcacgtat tatataagtg   1380

catttagtgg gctatttcga gcagttttca catacacgta attgagacta tcgtctccac   1440

cttgtattcc tcttcttcat agtgaatttc ctctctctgc ccgtggtttt tcccatggag   1500

ggtttccacg taaatatgtg tgttcttctt gtttttattt tgcttgtggt attgcctatt   1560

ctgtccgatc ataacaactc caaatatatt tgttcaaaac tggaaggatg gtcgaaggag   1620

tatggagagt ttttcgagcc ttgtgcatac ttagtcgaac gaacttccaa gagatgttct   1680

ttggtgagaa attgttaatt ttcttgaaca cctgaaatga aacaactacg agaaaatgga   1740

ttggcaaaca ctattgtttg acgaattgca tcacgtgttg ctgacagaag acaaaaggat   1800

caatttgata ataaatatga ccggtatgtt gggtcctaac aacaacaatt ggattgatct   1860

tttgctaatt gaggagtttc acacgtc                                        1887
```

<210> SEQ ID NO 36
<211> LENGTH: 782
<212> TYPE: DNA
<213> ORGANISM: Capsicum baccatum

<400> SEQUENCE: 36

```
cacaatgctt agcagttccg ctgtttctct ctaattgtat ccgttcaaaa atacaagctt     60

gtgacagatg aatcttagac tctctgacta cttgtaattc tatctacaat ttagccatct    120

ttctctatca tttgcttttg aaatggagtg acatgaacaa tgaggattca ttcattcagt    180

cgatctccac ttgctttgca ttgaggagtt ttttctctat catttgcttg agagttcaag    240

tgtctgggat ggacaatgtg gtcgttaaca ttgcctcttc tcatccaggt ttgttctttt    300

gcttcttaac tgaggggtat ttcttggttc cggagaatct ttttttggt aactaacata     360

ttcattttat taccaaagta atattacaaa tcaactacca gcctgatgac acaacctggt    420

agactcaaag aagaacccta ctgatcagac taataataat gaggatagta gtttagatca    480

ttgatcacag ctgctaactt atgcctaaca gtagcaatac aaataacatc ctgaaatact    540

agcctaacca ctttctccgg tgtagtactg attgtcctga caatcctaca attcctatca    600

tgccatatat ggtaaacgca tgcagcagta ccatcctgaa tatgtgttga ggctgatcga    660

cctttgacat tgttctcaat ccactcaagt tcactggacc aagccaaagc aatcctttga    720

atctttatcc agccgagcaa agcattccca cagtttagca gcatagctac acctaaagaa    780

ct                                                                   782
```

*BACCATUM CYTOPLASMIC* MALE STERILITY WITH FEMALE FERTILE FLOWERS IN *CAPSICUM ANNUUM*

CROSS-REFERENCE TO RELATED APPLICATIONS

This application claims the benefit of priority of U.S. Provisional Appl. Ser. No. 62/690,722, filed Jun. 27, 2018, the disclosure of which is hereby incorporated by reference in its entirety.

INCORPORATION OF SEQUENCE LISTING

The sequence listing that is contained in the file named "SEMB034US-revised_ST25.txt", which is 48.4 kilobytes as measured in Microsoft Windows operating system and was created on Oct. 11, 2022, is filed electronically herewith and incorporated herein by reference.

FIELD OF THE INVENTION

The present invention relates to the field of agriculture and more specifically to methods and compositions for producing pepper plants exhibiting uniform female fertility.

BACKGROUND OF THE INVENTION

The goal of vegetable breeding is to combine various desirable traits in a single variety/hybrid. Production of hybrid peppers may be carried out by hand-emasculation or by using male sterility. A number of male sterility systems have been identified for use in pepper production, however each system has limitations. Efforts to overcome these limitations are hindered by a lack of specific markers linked to the alleles associated with male sterility phenotypes. The use of marker-assisted selection (MAS) in plant breeding methods has made it possible to select plants based on genetic markers linked to traits of interest. However, accurate markers for identifying or tracking desirable traits in plants are frequently unavailable even if a gene associated with the trait has been characterized. These difficulties are further complicated by factors such as polygenic or quantitative inheritance, epistasis and an often incomplete understanding of the genetic background underlying expression of a desired phenotype.

SUMMARY OF THE INVENTION

In one aspect, the present invention provides a *Capsicum annuum* plant comprising a chromosomal segment from *Capsicum baccatum* on chromosome 6, wherein said chromosomal segment comprises an allele that confers female fertility in a male sterile *Capsicum annuum* plant having a *Capsicum baccatum* cytoplasm relative to a plant lacking said chromosomal segment. In some embodiments, the chromosomal segment is flanked by Marker M12 (SEQ ID NO: 12) and Marker M36 (SEQ ID NO: 36) in said plant. In further embodiments, the chromosomal segment is flanked by Marker M7 (SEQ ID NO: 7) and Marker M17 (SEQ ID NO: 17) in said plant. In some embodiments, the chromosomal segment is located between 428,143 bp and 3,500,133 bp on the public pepper CM334 v1.55 map.

The present invention also provides a seed that produces a *Capsicum annuum* plant comprising a chromosomal segment from *Capsicum baccatum* on chromosome 6, wherein said chromosomal segment comprises an allele that confers female fertility in a male sterile *Capsicum annuum* plant having a *Capsicum baccatum* cytoplasm relative to a plant lacking said chromosomal segment.

Additionally, the present invention provides a plant part of a *Capsicum annuum* plant comprising a chromosomal segment from *Capsicum baccatum* on chromosome 6, wherein said chromosomal segment comprises an allele that confers female fertility in a male sterile *Capsicum annuum* plant having a *Capsicum baccatum* cytoplasm relative to a plant lacking said chromosomal segment. In certain embodiments, the plant part is a cell, a seed, a root, a stem, a leaf, a flower, a fruit, or pollen.

In another aspect, the present invention provides a method for producing a *Capsicum annuum* plant that confers uniform female fertility in a male sterile *Capsicum annuum* plant having a *Capsicum baccatum* cytoplasm, comprising introgressing into said plant a chromosomal segment from *Capsicum baccatum* on chromosome 6 that confers uniform female fertility in a male sterile *Capsicum annuum* plant having a *Capsicum baccatum* cytoplasm relative to a plant lacking said chromosomal segment. In some embodiments, said introgressing comprises crossing a plant comprising said chromosomal segment with itself or with a second *Capsicum annuum* plant of a different genotype to produce one or more progeny plants; and selecting a progeny plant comprising said chromosomal segment. In further embodiments, wherein selecting a progeny plant comprises detecting at least one allele flanked by Marker M12 (SEQ ID NO: 12) and Marker M36 (SEQ ID NO: 36) on chromosome 6. In other embodiments, the progeny plant is an $F_2$-$F_6$ progeny plant. In particular embodiments, the crossing comprises backcrossing, which in certain embodiments comprises from 2-7 generations of backcrosses.

The present invention also provides a *Capsicum annuum* plant produced by a method comprising introgressing into said plant a chromosomal segment from *Capsicum baccatum* on chromosome 6 that confers uniform female fertility in a male sterile *Capsicum annuum* plant having a *Capsicum baccatum* cytoplasm relative to a plant lacking said chromosomal segment. Thus, the present invention also provides a method of producing food or feed comprising obtaining a *Capsicum annuum* plant comprising a chromosomal segment from *Capsicum baccatum* on chromosome 6, wherein said chromosomal segment comprises an allele that confers female fertility in a male sterile *Capsicum annuum* plant having a *Capsicum baccatum* cytoplasm relative to a plant lacking said chromosomal segment, or a part thereof, and producing said food or feed from said plant or part thereof.

In another aspect, the present invention provides a *Capsicum annuum* plant obtainable by a method comprising the step of introgressing into a plant a uniform female fertility phenotype allele from *Capsicum baccatum*, wherein said uniform female fertility phenotype allele is defined as located in a chromosomal segment flanked by Marker M12 (SEQ ID NO: 12) and Marker M36 (SEQ ID NO: 36) on chromosome 6. In some embodiments, the chromosomal segment is flanked by Marker M7 (SEQ ID NO: 7) and Marker M17 (SEQ ID NO: 17) on chromosome 6. In certain embodiments, the introgressing comprises backcrossing. In other embodiments, the introgressing comprises marker-assisted selection.

The present invention also provides a method of selecting a *Capsicum annuum* plant exhibiting uniform female fertility, comprising crossing a *Capsicum annuum* plant comprising a chromosomal segment from *Capsicum baccatum* on chromosome 6, wherein said chromosomal segment comprises an allele that confers female fertility in a male sterile

*Capsicum annuum* plant having a *Capsicum baccatum* cytoplasm relative to a plant lacking said chromosomal segment with itself or with a second *Capsicum annuum* plant of a different genotype to produce one or more progeny plants; and selecting a progeny plant comprising said chromosomal segment. In some embodiments, the selecting said progeny plant comprises identifying a genetic marker genetically linked to said chromosomal segment. In other embodiments, the selecting said progeny plant comprises identifying a genetic marker within or genetically linked to said chromosomal segment flanked in the genome of said plant by Marker M12 (SEQ ID NO: 12) and Marker M36 (SEQ ID NO: 36) on chromosome 6. In some embodiments, the progeny plant is an $F_2$-$F_6$ progeny plant. In particular embodiments, the crossing comprises backcrossing.

In yet another aspect, the present invention provides a cytoplasmic male sterile *Capsicum annuum* plant comprising a chromosomal segment from *Capsicum baccatum* on chromosome 6 that confers uniform female fertility relative to a plant lacking said chromosomal segment. In an embodiment, the cytoplasmic male sterility is *Baccatum* cytoplasmic male sterility.

BRIEF DESCRIPTION OF THE DRAWINGS

FIG. 2: Fingerprinting data shows that male sterile BCMS lines are heterozygous for the Gf allele while completely sterile BCMS lines are homozygous for the gf allele.

DETAILED DESCRIPTION

Figure 1:
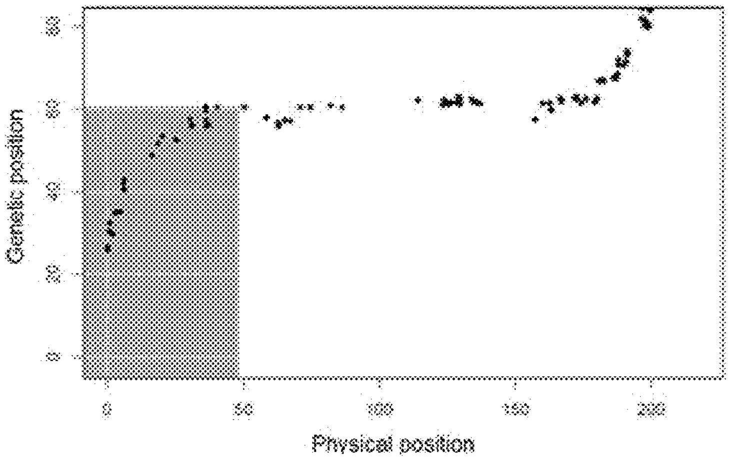
FIG. 1: The "Good Flowering" (GO locus from *Capsicum baccatum* maps to the short arm of chromosome 6, where it introduces suppressed recombination with the *Capsicum annuum* genome. "Good flowers" are defined as being male sterile but female fertile while "bad flowers" are defined as being male sterile and almost completely female sterile.

Male sterility is used by breeders for two basic product concepts in a variety of crops. The first product concept is seedless fruit. Plants comprising the male sterility trait are crossed with plants comprising parthenocarpy genes to produce hybrid seed. This hybrid seed produces plants bearing seedless fruit. Under normal circumstances, male sterile plants cannot set fruit in the absence of pollination. However, if the plant also contains parthenocarpy genes, then fruit set occurs in the absence of pollination. In this product concept, it is possible to use different forms of male sterility without a restorer locus. However, only cytoplasmic male sterility will allow for production of seed from which 100% of the plants grown from this seed are sterile and bear seedless fruit. Using genic male sterility for this product concept requires an intermediate seedling selection step after showing the hybrid seed, followed by transplanting or grafting of the selected sterile plants. The second product concept is one where male sterility is used to easily develop hybrid seed. In the development of hybrid seed it is important to ensure genetic purity of a seed batch. This entails minimizing the number of seed that are the result of self-fertilization. Self-fertilization is prevented during seed production through physical removal of male sex organs in the flower before the flower opens, a process referred to as emasculation. This is a labor-intensive procedure that is not only costly, but also is not 100% effective. Genetic emasculation of the female line overcomes these limitations and ensures the genetic purity of the hybrid seed. However, successful hybrid production requires that the male sterility system used can be restored in the hybrid. Thus, the male parent of the hybrid will typically contain a dominant male fertility restorer locus. When a male parent comprising the restorer locus is crossed with the male sterile female parent, fully fertile hybrid plants will be produced. Given that resultant hybrid plants are heterozygous, it is essential that the restorer locus be dominant.

Genetic (or genic) male sterility (GMS) systems utilize male sterility loci that are often inherited in a recessive manner and encoded within the nuclear genome. An exception to this is, for example, a GMS system in rapeseed where both the sterility and sterility suppressor genes are dominant. A primary disadvantage with the genetic male sterility system is that only half of the progeny plants will be male sterile. A breeder would therefore have to select which plants are suitable for hybrid/seedless fruit production post-germination, resulting in at least half of the seedlings being discarded. A system that does not have this problem is the cytoplasmic male sterility (CMS) system. In this system, the male sterility loci are coded in the mitochondrial DNA and, in the absence of a nuclear male fertility restoration gene, 100% of the progeny plants are male sterile. In pepper, the Peterson's CMS system is widely used because a dominant male fertility restoration locus is available, making this system suitable for both hybrid production and the seedless fruit concept. The restorer locus for Peterson's CMS is often referred to as the CMS restorer locus. The CMS restorer allele (Rf) was identified in pungent *Capsicum annuum* germplasm and has been mapped to a locus on the short arm of chromosome 6. Transferring a functioning restorer locus to sweet pepper types has proven difficult and remains the subject of much study and breeding efforts because the Peterson's CMS system is known to be unstable with respect to environmental conditions and genetic background.

An environmentally-stable alternative to the Peterson's CMS system is the *Baccatum* cytoplasmic male sterility (BCMS) system. This system was created by crossing a female *Capsicum baccatum* plant with a male *Capsicum annuum* plant. The resulting hybrid, which was obtained through a step of embryo rescue, contained a *Capsicum baccatum* cytoplasm and was male sterile. Through extensive backcrossing to the *Capsicum annuum* parent, the *Capsicum baccatum* genome was replaced with *Capsicum*

*annuum* DNA. However, the BCMS system has some limitations. First, female sterility segregates within the population of BCMS lines and efforts to eliminate this negative trait through crossing and selection has not been successful. Second, a dominant restorer locus for the BCMS system was not known, in the absence of a nuclear male fertility restoration gene.

The present inventors have found that the problem of unpredictable female sterility can be overcome by use of a chromosomal segment from *Capsicum baccatum* on the short arm of chromosome 6 that confers uniform female fertility in BCMS pepper lines. The invention therefore provides methods and compositions for conferring uniform female fertility in pepper plants, as well as markers for tracking and identifying the novel chromosomal segment in plants during breeding. A non-limiting summary of useful markers is provided in Table 1. The chromosomal segment is located between markers M12 (SEQ ID NO: 12) and M36 (SEQ ID NO: 36), while markers M1-M3, M5-M11, and M13-M35 can also be used to select the chromosomal segment in subsequent germplasm. The specific selected markers used depends on the non-donor parent. Therefore, a combination of markers listed in Table 1 may be used for benefit in a first selection, while markers can be limited to a polymorphic subset in a given cross for further selections.

The limitation of use of the BCMS system due to the lack of a dominant restorer locus has also been overcome through identification of a novel male fertility restoration locus for use in the BCMS system. The identification of this locus and genetic markers associated with the locus is described in U.S. Provisional Appln. Ser. No. 62/690,728, filed concurrently herewith, the disclosure of which is incorporated herein by reference in its entirety.

I. Genomic Regions, Alleles, and Polymorphisms Associated with Uniform Female Fertility The inventors surprisingly identified a novel chromosomal segment on chromosome 6 from *Capsicum baccatum* that provides uniform female fertility in a *Baccatum* cytoplasmic male sterile plant, together with polymorphic nucleic acids and linked markers for tracking and introgressing the chromosomal segment into potentially any variety during plant breeding.

The newly identified chromosomal segment on chromosome 6 covers a region of 31.7 cM and is flanked by marker M12, a SNP change [C/A] at 26,405 bp, on genome sequence version 1.55 of pepper line CM334, which can be found at solgenomics.net, and marker M36, a SNP change [C/G] at 21,133,217 bp. Interstitial markers, such as M8, a SNP change [C/T] at 87,022 bp, M10, a SNP change [T/C] at 89,795 bp, M9, a SNP change [T/C] at 125,861 bp, M11, a SNP change [TIC] at 386,489 bp, M5, a SNP change [A/G] at 427,257 bp, M7, a SNP change [A/G] at 428,143 bp, M6, a SNP change [A/C] at 428,207 bp, M15, a SNP change [TIC] at 2,999,718 bp, M14, a SNP change [A/C] at 3,009,771 bp, M13, a SNP change [A/G] at 3,055,268 bp, M1, a SNP change [A/G] at 3,064,350 bp, M3, a SNP change [G/T] at 704,163 bp, M2, a SNP change [G/A] at 3,064,557 bp, M19, a SNP change [T/C] at 3,308,938 bp, M21, a SNP change [T/G] at 3,422,765 bp, M20, a SNP change [A/G] at 3,475,770 bp, M17, a SNP change [C/A] at 3,500,133 bp, M16, a SNP change [T/G] at 3,504,248 bp, M18, a SNP change [G/A] at 3,505,583 bp, M26, a SNP change [A/T] at 4,240,551 bp, M23, a SNP change [G/A] at 4,240,789 bp, M24, a SNP change [G/C] at 4,245,699 bp, M22, a SNP change [T/A] at 4,276,008 bp, M25, a SNP change [G/A] at 70,994,266 bp, M28, a SNP change [G/A] at 6,240,565 bp, M29, a SNP change [TIC] at 6,241,544 bp, M27, a SNP change [G/A] at 7,226,809 bp, M31, a SNP change [G/T] at 8,522,155 bp, M30, a SNP change [A/G] at 8,522,245 bp, M34, a SNP change [G/T] at 10,664,630 bp, M33, a SNP change [T/C] at 10,670,362 bp, M32, a SNP change [A/T] at 10,971,807 bp, and M35, a SNP change [TIC] at 11,108,817 bp, can be used in addition to the flanking markers to select for the uniform female fertility QTL on chromosome 6. Thus, the present disclosure provides a *Capsicum annuum* plant comprising a chromosomal segment from *Capsicum baccatum* on chromosome 6 of *Capsicum annuum* flanked by markers M12 and M36 that confers uniform female fertility to BCMS pepper plants. In certain embodiments, one or both of the flanking markers are interstitial markers between M12 and M36, such as markers M8, M10, M9, M11, M5, M7, M6, M15, M14, M13, M1, M2, M3, M19, M21, M20, M17, M16, M18, M26, M23, M24, M22, M25, M28, M29, M27, M31, M30, M34, M33, M32, or M35, and comprise a *Capsicum baccatum* allele at said marker(s). In certain embodiments, the flanking markers of the chromosomal segment that confers uniform female fertility to BCMS plants are M7 and M17, or preferably M1 and M19. In some embodiments, the chromosomal segment from *Capsicum baccatum* on chromosome 6 of *Capsicum annuum* comprises a plurality of the markers listed in Table 1, including any possible combination thereof.

II. Introgression of Genomic Regions Associated with Uniform Female Fertility Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel markers for identifying and tracking introgression of one or more of the genomic regions from a *Capsicum baccatum* plant comprising uniform female fertility alleles into *Baccatum* CMS lines. Any *Capsicum baccatum* line may be used as a source for the uniform female fertility alleles described herein. One such example of such a *Capsicum baccatum* line is PI159242, which is available from USDA-ARS GRIN, National Plant Germplasm System, Beltsville, Md. USA. Other *Capsicum baccatum* lines, such as PI640880 and PI497974, may also be utilized, as described herein in Example 5. The invention further provides markers for identifying and tracking the novel introgression disclosed herein during plant breeding, including the markers set forth in Table 1.

Markers within or linked to any of the genomic intervals of the present invention can be used in a variety of breeding efforts that include introgression of genomic regions associated with uniform female fertility into a desired genetic background. For example, a marker within 30 cM, 25 cM, 20 cM, 16 cM, 15 cM, 10 cM, 5 cM, 2 cM, or 1 cM of a marker associated with uniform female fertility described herein can be used for marker-assisted introgression of genomic regions associated with a uniform female fertility phenotype.

Pepper plants comprising one or more introgressed regions associated with a desired phenotype wherein at least 10%, 25%, 50%, 75%, 90%, or 99% of the remaining genomic sequences carry markers characteristic of the germplasm are also provided. Pepper plants comprising an introgressed region comprising regions closely linked to or adjacent to the genomic regions and markers provided herein and associated with a uniform female fertility phenotype are also provided.

III. Development of Pepper Plants that Provide Uniform Female Fertility

For most breeding objectives, commercial breeders work within germplasm that is "cultivated type" or "elite." This germplasm is easier to breed because it generally performs well when evaluated for horticultural performance. For example, *Capsicum annuum* is an agronomically elite, cultivated pepper adapted to commercial use. However, the performance advantage a cultivated germplasm provides can be offset by a lack of allelic diversity. Breeders generally accept this tradeoff because progress is faster when working with cultivated material than when breeding with genetically diverse sources.

In contrast, when a breeder makes either intraspecific crosses, or interspecific crosses, a converse tradeoff occurs. In these examples, a breeder typically crosses germplasm of an economically important species with a non-cultivated or commercially unacceptable species. The breeder can gain access to novel alleles from the non-cultivated species, but may have to overcome genetic drag or interspecific hybridization barriers associated with such crosses. Because of the difficulty with this breeding strategy, this approach often fails because of fertility and fecundity problems. The difficulty with this breeding approach extends to many crops, and is exemplified with an important disease resistant phenotype that was first described in tomato in 1944 (Smith, *Proc. Am. Soc. Hort. Sci.* 44:413-16). In this cross, a nematode disease resistance was transferred from *L. peruvianum* (PI128657) into a cultivated tomato. Despite intensive breeding, it was not until the mid-1970's before breeders could overcome the genetic drag and release successful lines carrying this trait. Indeed, even today, tomato breeders deliver this disease resistance gene to a hybrid variety from only one parent. This allows the remaining genetic drag to be masked. The inventiveness of succeeding in this breeding approach has been recognized by the USPTO (U.S. Pat. Nos. 6,414,226, 6,096,944, 5,866,764, and 6,639,132)

The process of introgressing desirable genes from one species into another while avoiding problems with linkage drag or low heritability is a long and often arduous process. Success in deploying alleles derived from related species therefore strongly depends on minimal or truncated introgressions that lack detrimental effects and reliable marker assays that replace phenotypic screens. Success is further defined by simplifying genetics for key attributes to allow focus on genetic gain for quantitative traits. Moreover, the process of introgressing genomic regions from non-cultivated lines or different species can be greatly facilitated by the availability of informative markers.

One of skill in the art would therefore understand that the alleles, polymorphisms, and markers provided by the invention allow the tracking and introduction of any of the genomic regions identified herein into any genetic background. In addition, the genomic regions associated with disease resistance disclosed herein can be introgressed from one genotype to another and tracked phenotypically or genetically. Thus, Applicants' discovery of accurate markers associated with uniform female fertility will facilitate the development of pepper plants having beneficial phenotypes.

For example, plants and seeds can be genotyped using the markers of the present invention in order to develop varieties comprising desired uniform female fertility. Moreover, marker-assisted selection (MAS) allows identification of plants which are homozygous or heterozygous the desired introgression.

Meiotic recombination is essential for plant breeding because it enables the transfer of favorable alleles across genetic backgrounds, the removal of deleterious genomic fragments, and pyramiding traits that are genetically tightly linked. In the absence of accurate markers, limited recombination forces breeders to enlarge segregating populations for progeny screens. Moreover, phenotypic evaluation is time-consuming, resource-intensive and not reproducible in every environment. The markers provided by the invention offer an effective alternative and therefore represent a significant advance in the art.

Phenotypic evaluation of large populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among pepper species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

Many desirable traits that are successfully introduced through introgression can also be introduced directly into a plant by the use of molecular techniques. One aspect of the invention includes plants with a genome that has been changed by any method using site-specific genome modification techniques. Techniques of site-specific genome modification include the use of enzymes such as, endonucleases, recombinases, transposases, helicases and any combination thereof. In one aspect, an endonuclease is selected from a meganuclease, a zinc-finger nuclease (ZFN), a transcription activator-like effector nucleases (TALEN), an Argonaute, and an RNA-guided nuclease, such as a CRISPR associated nuclease.

In another aspect, the endonuclease is a dCas9-recombinase fusion protein. As used herein, a "dCas9" refers to a Cas9 endonuclease protein with one or more amino acid mutations that result in a Cas9 protein without endonuclease activity, but retaining RNA-guided site-specific DNA binding. As used herein, a "dCas9-recombinase fusion protein" is a dCas9 with a protein fused to the dCas9 in such a manner that the recombinase is catalytically active on the DNA.

Non-limiting examples of recombinase include a tyrosine recombinase attached to a DNA recognition motif provided herein is selected from the group consisting of a Cre recombinase, a Gin recombinase a Flp recombinase, and a Tnp1 recombinase. In an aspect, a Cre recombinase or a Gin recombinase provided herein is tethered to a zinc-finger DNA-binding domain, or a TALE DNA-binding domain, or a Cas9 nuclease. In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

Site-specific genome modification enzymes, induce a genome modification such as a double-stranded DNA break (DSB) or single-strand DNA break at the target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of exogenous sequences by homologous recombination.

Another aspect of the invention includes transgenic plant cells, transgenic plant tissues, transgenic plants, and transgenic seeds that comprise the recombinant DNA molecules and engineered proteins provided by the invention. These cells, tissues, plants, and seeds comprising the recombinant DNA molecules and engineered proteins exhibit resistance to *P. capsici*. Suitable methods for transformation of host plant cells for use with the current invention include virtually any method by which DNA can be introduced into a cell (for example, where a recombinant DNA construct is stably integrated into a plant chromosome) and are well known in the art. An exemplary and widely utilized method for introducing a recombinant DNA construct into plants is the *Agrobacterium* transformation system, which is well known to those of skill in the art. Another exemplary method for introducing a recombinant DNA construct into plants is insertion of a recombinant DNA construct into a plant genome at a pre-determined site by methods of site-directed integration. Transgenic plants can be regenerated from a transformed plant cell by the methods of plant cell culture. A transgenic plant homozygous with respect to a transgene (that is, two allelic copies of the transgene) can be obtained by self-pollinating (selfing) a transgenic plant that contains a single transgene allele with itself, for example an R0 plant, to produce R1 seed. One fourth of the R1 seed produced will be homozygous with respect to the transgene. Plants grown from germinating R1 seed can be tested for zygosity, using a SNP assay, DNA sequencing, or a thermal amplification assay that allows for the distinction between heterozygotes and homozygotes, referred to as a zygosity assay.

IV. Molecular Assisted Breeding Techniques

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Vegetable breeders use molecular markers to interrogate a crop's genome and classify material based on genetic, rather than phenotypic, differences. Advanced marker technologies are based on genome sequences, the nucleotide order of distinct, polymorphic genotypes within a species. Such platforms enable selection for horticultural traits with markers linked to favorable alleles, in addition to the organization of germplasm using markers randomly distributed throughout the genome. In the past, a priori knowledge of the genome lacked for major vegetable crops that now have been sequenced. Scientists exploited sequence homology, rather than known polymorphisms, to develop marker platforms. Man-made DNA molecules are used to prime replication of genome fragments when hybridized pair-wise in the presence of a DNA polymerase enzyme. This synthesis, regulated by thermal cycling conditions that control hybridization and replication of DNA strands in the polymerase chain reaction (PCR) to amplify DNA fragments of a length dependent on the distance between each primer pair. These fragments are then detected as markers and commonly known examples include AFLP and RAPD. A third technique, RFLP does not include a DNA amplification step. Amplified fragment length polymorphism (AFLP) technology reduces the complexity of the genome. First, through digestive enzymes cleaving DNA strands in a sequence-specific manner. Fragments are then selected for their size and finally replicated using selective oligonucleotides, each homologous to a subset of genome fragments. As a result, AFLP technology consistently amplifies DNA fragments across genotypes, experiments and laboratories.

Polymorphisms comprising as little as a single nucleotide change can be assayed in a number of ways. For example, detection can be made by electrophoretic techniques including a single strand conformational polymorphism (Orita et al., *Genomics* 8:271-278, 1989), denaturing gradient gel electrophoresis (Myers, EP 0273085), or cleavage fragment length polymorphisms (Life Technologies, Inc., Gaithersburg, Md.), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer et al., *Biotechniques* 12:82-87, 1992), or PCR amplification of multiple specific alleles (PAMSA; Dutton and Sommer, *Biotechniques* 11:700-702, 1991).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a *Capsicum annuum* plant a genotype associated with uniform female fertility, identify a *Capsicum annuum* plant with a genotype associated with uniform female fertility, and to select a *Capsicum annuum* plant with a genotype associated with uniform female fertility. In certain embodiments of methods of the invention, polymorphic nucleic acids can be used to produce a *Capsicum annuum* plant that comprises in its genome an introgressed locus associated with uniform female fertility. In certain embodiments of the invention, polymorphic nucleic acids can be used to breed progeny *Capsicum annuum* plants comprising a locus associated with uniform female fertility.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e., for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with uniform female fertility in *Capsicum annuum* plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al., *Cold Spring Harbor Symp. Quant. Biol.* 51:263-273, 1986; European Patent 50,424; European Patent 84,796; European Patent 258,017; European Patent 237,362; European Patent 201,184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entirety. However, the compositions and methods of the present invention can be used in conjunction with any polymorphism typing method to type polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523, 2003; Cui et al., *Bioinformatics* 21:3852-3858, 2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

V. Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which *Capsicum annuum* plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "Quantitative Trait Locus (QTL)" is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, marker assisted selection, various plant transformation techniques and/or methods that provide for homologous recombination, non-homologous recombination, site-specific recombination, and/or genomic modifications that provide for locus substitution or locus conversion.

As used herein, the term "linked," when used in the context of nucleic acid markers and/or genomic regions, means that the markers and/or genomic regions are located on the same linkage group or chromosome such that they tend to segregate together at meiosis.

As used herein, "cytoplasmic male sterility" refers to plants that are not usually capable of breeding from self-pollination in absence of a male fertility restorer locus but are capable of breeding from being cross-pollinated when used as the female parent, and wherein the male sterility is the result of an incompatibility between the cytoplasm and the nuclear genome.

As used herein, "*Baccatum* cytoplasmic male sterility" or "BCMS" refers to cytoplasmic male sterile plants wherein the cytoplasm is from a *Capsicum baccatum* plant and the nuclear genome is from a *Capsicum annuum* plant.

As used herein, a "female parent" refers to a pepper plant that is the recipient of pollen from a male donor line, which pollen successfully pollinates an egg. A female parent can be any pepper plant that is the recipient of pollen. Such female parents can be male sterile, for example, because of genic male sterility, cytoplasmic male sterility, or because they have been subject to physical emasculation of the stamens. Genic or cytoplasmic male sterility can be manifested in different manners, such as sterile pollen, malformed or stamenless flowers, positional sterility, and functional sterility.

As used herein, "uniform female fertility" refers to the uniform production of male sterile flowers that are otherwise developmentally normal (i.e. female fertile) and produce viable fruit and seed if fertilized with a male fertile pollen source. A locus that confers uniform female fertility means that all flowers of a *Baccatum* cytoplasmic male sterile plant carrying the locus will comprise functioning female organs and non-functioning male organs in absence of a male fertility restoration locus.

As used herein, "good flower" refers to pepper plants comprising a flower that is female fertile and developmentally normal. Plants with good flowers can be male fertile or male sterile.

As used herein, "male parent plant" refers to a parent plant that provides pollen to (i.e. is a pollinator for) a female line. They may be useful for breeding of progeny pepper plants, such as parthenocarpic seedless progeny plants.

As used herein, "resistance allele" means the nucleic acid sequence associated with resistance or tolerance to disease.

As used herein "resistance" or "improved resistance" in a plant to disease conditions is an indication that the plant is less affected by disease conditions with respect to yield, survivability and/or other relevant agronomic measures, compared to a less resistant, more "susceptible" plant. Resistance is a relative term, indicating that a "resistant" plant survives and/or produces better yields in disease conditions compared to a different (less resistant) plant grown in similar disease conditions. As used in the art, disease "tolerance" is sometimes used interchangeably with disease "resistance." One of skill will appreciate that plant resistance to disease conditions varies widely, and can represent a spectrum of more-resistant or less-resistant phenotypes. However, by simple observation, one of skill can generally determine the relative resistance or susceptibility of different plants, plant lines or plant families under disease conditions, and furthermore, will also recognize the phenotypic gradations of "resistant."

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

VI. Examples

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1. Creation of a BCMS *Capsicum annuum* Plant

The compatibility between *Capsicum annuum* and *Capsicum baccatum* for interspecific crosses is very low. To transfer genetic information between these two species, intermediate pepper species, such as *Capsicum chinense* or *Capsicum frutescens*, have been used as a 'genetic bridge'. However, this method only allows for the transfer of nuclear traits. To develop a BCMS plant where a *Capsicum annuum* genome is introduced into a *Capsicum baccatum* cytoplasm, it is necessary to pollenate a *Capsicum baccatum* flower with *Capsicum annuum* pollen. These combinations typically never led to viable hybrid seed and it was therefore necessary to use embryo rescue techniques to recover a *Capsicum baccatum* x *Capsicum annuum* hybrid. The method described herein was used to develop *Capsicum baccatum* x *Capsicum annuum* hybrids from several *Capsicum baccatum* accessions, such as PI497974, PI159242, and PI640880.

Plants of these *Capsicum baccatum* accessions were grown simultaneously with *Capsicum annuum* lines that served as pollen donors. Flowers on the *Capsicum baccatum* plants were emasculated before the anthers shed and subsequently pollinated with the *Capsicum annuum* pollen. One day after the first pollination, the pollinated flowers were dipped in 200 mg/L NAA (1-naphthylacetic acid) followed by a second pollination after the NAA solution (growth regulator) had dried. The flowers were then left to develop fruit. Ripe fruit were harvested, and seeds were extracted from the fruit for embryo rescue. The embryo rescue was performed under aseptic conditions by dissecting the embryos from endosperms. The extracted embryos were cultured on MS media until seedlings had fully developed. These $F_1$ seedlings were checked for *Capsicum baccatum* x *Capsicum annuum* hybridization using polymorphic DNA markers. Seedlings that were true hybrids were selected for further backcrossing to the *Capsicum annuum* parent. Early backcross generations were selected phenotypically for male sterility and the *Capsicum annuum* recurrent parent phenotype and the genome was evaluated for *Capsicum annuum* percentage using polymorphic DNA markers. In later generations, additional horticultural traits were used to select plants for advancement.

Example 2. Identification of the Good Flowering (GO Locus in *Capsicum baccatum*

Male sterile flowers have reduced anther development and no viable pollen, but otherwise have relatively normal anatomy. Male sterile flowers can produce viable fruit and seed if plants are fertilized with a fertile pollen source. Completely sterile flowers are both male and female sterile and have enlarged carpel structure and reduced petal development. The completely sterile flowers in the *Baccatum* CMS (BCMS) system have been designated "bad flowers", while the male sterile/female fertile flowers have been designated as "good flowers". In BCMS lines, the bad flowers trait segregates within the population, persisting in advanced backcross lines derived from as many as 15 generations of backcrossing to *Capsicum annuum*. Thus, the bad flowers trait can not be eliminated through backcrossing. Furthermore, the segregation ratio is not stable, as the proportion of bad flowers in a population can range from 0% to 50%, depending on the genotype and environment. This suggests that the nuclear allele(s) required to maintain female fertility in flowers that are male sterile in the presence of the *Capsicum baccatum* cytoplasm are inherited from *Capsicum baccatum*.

A $BC_1$ population was identified to segregate approximately 1:1 for good flowers and bad flowers, where good flowers are female fertile male sterile flowers and bad flowers are completely sterile flowers. This population was used to map loci associated with the good flowering (Gf) trait. Using genetic linkage mapping, where the Gf trait was coded as a dominant marker phenotype, the Gf trait was mapped to the short arm of chromosome 6, between the map positions of 25.7 cM and 40.8 cM (FIG. 1). The Gf locus explained 100% of the variation observed for the flowering phenotype, and was found to be completely dominant, with the Gf allele from *Capsicum baccatum* conferring female fertility in male sterile flowers. In this cross, recombination was completely suppressed within this genomic region, as evidenced by comparing the de-novo linkage map created from this population to the consensus map (FIG. 1).

Example 3. Validation of the Good Flowering Locus

If the *Capsicum baccatum* Gf allele is required for good flower development and successful reproduction in the presence of the *Capsicum baccatum* cytoplasm, then all BCMS lines developed in the backcross breeding effort would need to be maintained in the heterozygous state at the Gf locus (Gf allele from *Capsicum baccatum* and gf allele from *Capsicum annuum*). To confirm the Gf locus as responsible for the segregation of good (female fertile/male sterile) and bad (completely sterile) flowers across all BCMS lines, a panel of diverse BCMS lines were fingerprinted. Ten plants from each of the 18 advanced BCMS lines were grown and phenotyped for good and bad flowers in the greenhouse. Leaf tissue was bulked from good or bad flowering plants separately for each line and submitted for fingerprinting. Not all populations segregated for the bad flowering trait, so tissue was bulked for only good flowering plants in these lines. FIG. 2 shows that the region described on the short arm of chromosome 6 is heterozygous (Gfgf) for good flowering plants and homozygous (gfgf) for bad flowering plants across BCMS lines. Therefore, it was concluded that the Gf locus confers female fertility in plants across all BCMS backgrounds. FIG. 2 also shows that the smallest region containing the Gf locus ends at marker M36. Fine mapping of the locus was complicated by a significant reduction in recombination rate in the introgressed region. To overcome this, a large volume of plants needed to be screened to identify recombinants within the introgressed region. An additional 15,269 plants were developed and genotypically screened for recombination events in the introgressed region. A small subset of recombinants were identified and used to further map the locus. Fine mapping placed the Gf locus in a 5.3 cM region between markers M7 and M17. One experiment suggested that the Gf locus was in a region of 3.9 cM between markers M1 and M19.

Figure 3:
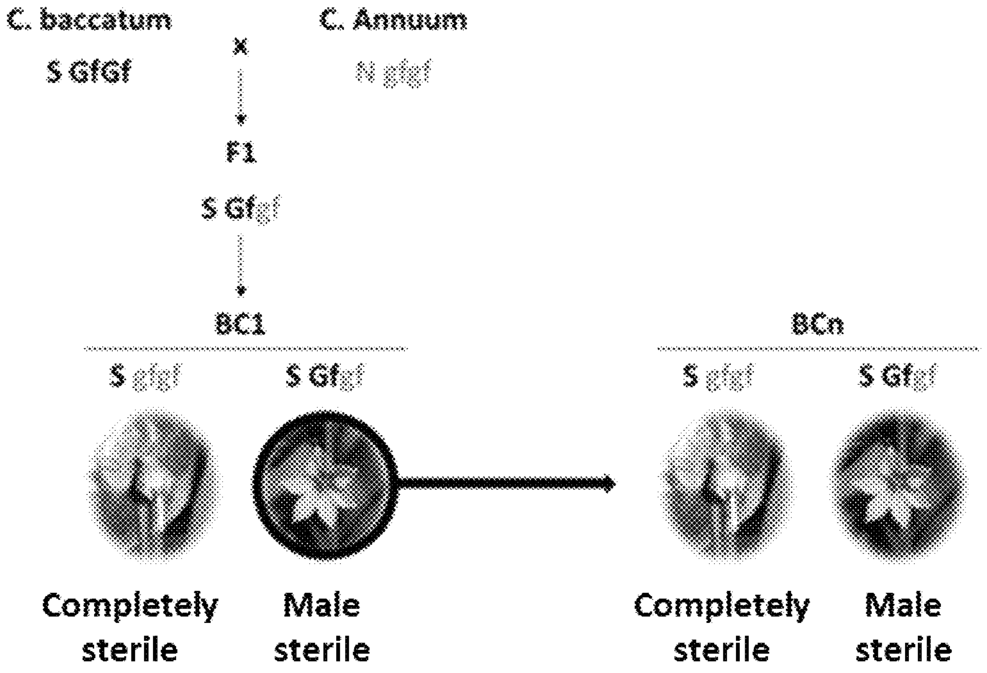
FIG. 3: Shows a crossing scheme explaining why completely sterile plants could not be eliminated from a *Capsicum baccatum* x *Capsicum annuum* cross through normal backcrossing to the *Capsicum annuum* parent. The plants having a gfgf genotype with *Capsicum baccatum* cytoplasm (S) are sterile and do not contribute to next backcross generation. While the male sterile offspring cannot be selfed and is always crossed with the gfgf genotype of the *Capsicum annuum* parent making it impossible to fix the Gf locus through normal backcrossing and selection. The pictures shown with the genotypes show the flower phenotype for that genotype.

The results obtained from the mapping and fingerprint experiments is consistent with the observed segregation patterns and confirms the genetic model that explains why continued backcrossing to *Capsicum annuum* fails to eliminate completely sterile flowers, resulting in segregation in each generation (FIG. 3).

Plants with a *Capsicum baccatum* cytoplasm (S) are completely male sterile and almost completely female sterile when the genotype of the Gf locus is homozygous recessive (gfgf) and do not contribute to next backcross generation. Furthermore, the alleles at the Gf locus appear to confer different levels of zygotic and embryonic fitness in the presence of *Capsicum baccatum* cytoplasm. Fitness appears to follow the relationship: GfGf>Gfgf>gfgf. This explains the segregation distortion in favor of the Gf allele that is observed in different populations. In backcross CMS lines, the frequency of gfgf ranges from 0-50%, indicating segregation distortion in favor of Gfgf gametes.

Example 4. Fixing and Tracking the Gf Allele in Pepper Plants

Figure 4:
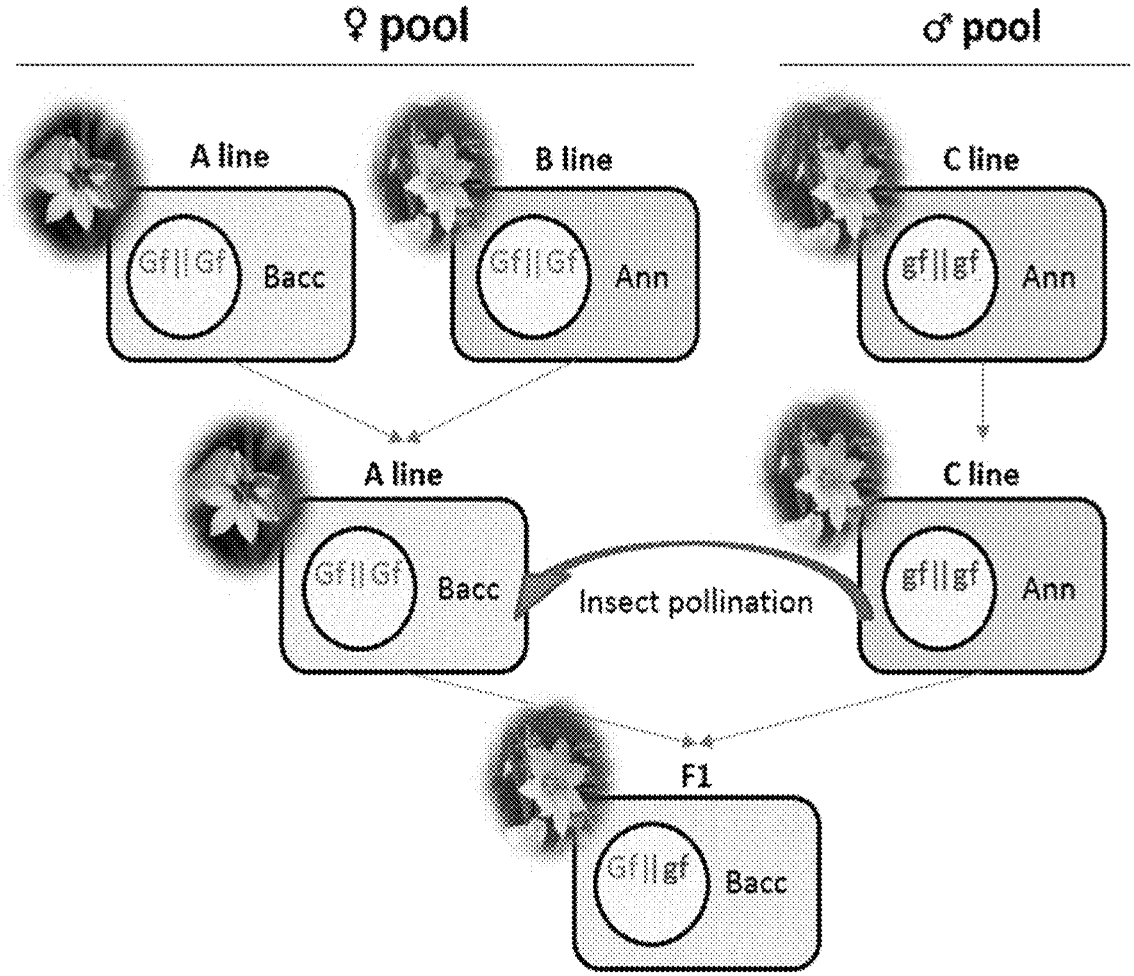
FIG. 4: Shows a schematic of the hybrid production concept with CMS, based on *Capsicum baccatum* cytoplasm. The female pool comprises two lines that lack the male fertility restorer locus: the A-line, which is a male sterile line that serves as the female parent in the hybrid cross; and the B-line, which is a male fertile line that serves as the maintainer and enables crosses within the female breeding pool. The C-line serves as the male parent of the hybrid cross and generally is a normal *Capsicum annuum* line that lacks the Gf locus, but is fixed for the male fertility restorer locus allele Rf. "Bacc" indicates plants with a *Capsicum baccatum* cytoplasm, while "Ann" indicates plants with a *Capsicum annuum* cytoplasm.

The male sterile nature of BCMS lines renders it impossible to obtain GfGf BCMS plants through selfing, nor will backcrossing with the fertile *Capsicum annuum* line lead to a fixed Gf allele. Obtaining GfGf plants in the female breeding pool requires the Gf allele to be homozygous in both the A-line (male sterile female with *Capsicum baccatum* cytoplasm) and the B-line (male fertile female "maintainer line" with *Capsicum annuum* cytoplasm) (FIG. 4). Since the only source of Gf is the male sterile A-line, it was necessary to find a way to transfer the Gf allele from the A-lines to the B-line. The A-line had to function as the male parent to transfer the Gf allele to the B-line, while maintaining the *Capsicum annuum* cytoplasm of the B-line. To use the A-line as a male parent, it was necessary to obtain BCMS plants that showed restored male fertility. At the time this was conducted, the genetics of the male fertility restoration locus for *Capsicum baccatum*-based CMS was unknown. Therefore, plants from BCMS populations that segregated for male fertility were used as Gf donors for the B-line. The B-line was subsequently selfed to fix the Gf allele in the B-line. The only method of determining the presence of the Gf allele is through use of molecular markers as, phenotypically, all plants were fully fertile and had good flowers, irrespective of the genetic configuration at the Gf locus. This is unexpected, based on the complete sterility of plants having a *Capsicum baccatum* cytoplasm but homozygous for the *Capsicum annuum* fertility allele (gf). It was expected that plants having a *Capsicum annuum* cytoplasm and homozygous for the *Capsicum baccatum* fertility allele (Gf) would have the same deleterious nuclear-cytoplasm interaction leading to complete sterility. However, the combination of GfGf with *Capsicum annuum* cytoplasm leads to normal fertility. A list of markers, of which a subset is polymorphic in the region the Gf locus is located, are given in Table 1. After fixing the Gf locus in the B-line it became possible to fix the Gf locus in the A-line through a backcross between the A-line and the B-line, resulting in offspring that is homozygous for the Gf locus.

TABLE 1

List of markers and favorable alleles at each marker for tracking the Gf locus

| Marker Name | Marker Sequence (SEQ ID NO) | Favorable Allele | *Capsicum annuum* Genetic Position (cM) | Public position SNP CM334v1.55 (bp) | SNP Position in Marker (bp) | SNP change |
|---|---|---|---|---|---|---|
| M12 | 12 | A | 0.01 | 26,405 | 1149 | C/A |
| M8 | 8 | T | 0.14 | 87,022 | 117 | C/T |
| M10 | 10 | C | 0.15 | 89,795 | 484 | T/C |
| M9 | 9 | C | 0.23 | 125,861 | 93 | T/C |
| M11 | 11 | C | 0.79 | 386,489 | 313 | T/C |
| M5 | 5 | G | 0.88 | 427,257 | 151 | A/G |
| M7 | 7 | G | 0.88 | 428,143 | 287 | A/G |
| M6 | 6 | C | 0.88 | 428,207 | 151 | A/C |
| M15 | 15 | C | 1.76 | 2,999,718 | 330 | T/C |
| M14 | 14 | C | 1.78 | 3,009,771 | 387 | A/C |
| M13 | 13 | G | 1.88 | 3,055,268 | 188 | A/G |
| M1 | 1 | G | 1.90 | 3,064,350 | 358 | A/G |
| M3 | 3 | T | 2.73 | 704,163 | 151 | G/T |
| M2 | 2 | A | 1.90 | 3,064,557 | 151 | G/A |
| M19 | 19 | C | 5.76 | 3,308,938 | 523 | T/C |
| M21 | 21 | G | 6.00 | 3,422,765 | 592 | T/G |
| M20 | 20 | G | 6.11 | 3,475,770 | 779 | A/G |
| M17 | 17 | A | 6.17 | 3,500,133 | 41 | C/A |
| M16 | 16 | G | 6.18 | 3,504,248 | 294 | T/G |
| M18 | 18 | A | 6.18 | 3,505,583 | 98 | G/A |
| M26 | 26 | T | 7.75 | 4,240,551 | 287 | A/T |
| M23 | 23 | A | 7.75 | 4,240,789 | 534 | G/A |
| M24 | 24 | C | 7.76 | 4,245,699 | 279 | G/C |
| M22 | 22 | A | 7.83 | 4,276,008 | 279 | T/A |
| M25 | 25 | A | 14.74 | 70,994,266 | 49 | G/A |
| M28 | 28 | A | 16.56 | 6,240,565 | 275 | G/A |
| M29 | 29 | C | 16.56 | 6,241,544 | 30 | T/C |
| M27 | 27 | A | 19.43 | 7,226,809 | 151 | G/A |
| M31 | 31 | T | 21.97 | 8,522,155 | 151 | G/T |
| M30 | 30 | G | 21.97 | 8,522,245 | 151 | A/G |
| M34 | 34 | T | 26.03 | 10,664,630 | 142 | G/T |
| M33 | 33 | C | 26.04 | 10,670,362 | 246 | T/C |
| M32 | 32 | T | 26.52 | 10,971,807 | 151 | A/T |
| M35 | 35 | C | 26.72 | 11,108,817 | 1613 | T/C |
| M36 | 36 | G | 35.72 | 21,133,217 | 285 | C/G |

Example 5. Determining the Presence of the Gf Locus in Multiple *Capsicum baccatum* Lines Additional *Capsicum baccatum* lines were screened to determine whether the Gf locus is unique to *Capsicum baccatum* line PI159242 or can be obtained from other *Capsicum baccatum* lines. New BCMS lines were developed using *Capsicum baccatum* lines PI640880 and PI497974 as CMS donors by following the same protocol as described in Example 1. Offspring produced from embryo rescue recovered BCMS lines and the CMS donors were tested with markers. Furthermore, different plant selections were used to test the presence/absence of good and bad flowers, where good flowers are male sterile flowers with normal female fertility, which is determined based on phenotype and bad flowers are almost completely sterile flowers (FIG. 3). These plant selections were derived from a backcross to the recurrent parent and one would thus only find plants with the genotypes of Gfgf and gfgf. Table 2 shows that the haplotype in the Gf region is the same for all donors based on the markers tested. Furthermore, the plants of the BCMS offspring containing a *Capsicum baccatum* allele at markers M40, M9, and M25 all showed the desired male sterile/female fertile flower phenotype that is expected from the presence of the Gf allele. This demonstrates that the Gf allele is not unique to *Capsicum baccatum* line PI159242 and can be found in other *Capsicum baccatum* accessions.

TABLE 2

A summary of genotype and flower phenotype for BCMS plants derived from three different *Capsicum baccatum* accessions

| Plant selection | Plant selection | Genotype | n plants | n good flower | n bad flower | M40 | M9 | M25 | M35 | M36 | M37 | M38 | M39 |
|---|---|---|---|---|---|---|---|---|---|---|---|---|---|
| CMS Donor 1 = Pl159242 | | | | | | TT | TT | GG | TT | CC | GG | AA | TT |
| Recurrent Parent | | | | | | CC | CC | AA | CC | GG | AA | TT | AA |
| BCMS Family Donor 1 | Line 1 | bac/ann | | | | CT | CT | AG | CT | CG | AG | AA | TT |
| BCMS Family Donor 1 | Line 1 | ann/ann | | | | CC | CC | CC | CC | CC | CC | CC | CC |
| CMS Donor 2 = Pl640880 | | | | | | TT | TT | GG | TT | CC | GG | AA | TT |
| Recurrent Parent | | | | | | CC | CC | AA | CC | GG | AA | TT | AA |
| BCMS Family Donor 2 | Line 1 | bac/ann | 29 | 24 | 0 | CT | CT | AG | TT | CC | GG | AA | TT |
| BCMS Family Donor 2 | Line 1 | ann/ann | 26 | 0 | 14 | TT | TT | GG | TT | CC | GG | AA | TT |
| BCMS Family Donor 2 | Line 2 | bac/ann | 24 | 20 | 0 | CT | CT | AG | TT | CC | GG | AA | TT |
| BCMS Family Donor 2 | Line 2 | ann/ann | 24 | 2 | 12 | TT | TT | GG | TT | CC | GG | AA | TT |
| BCMS Family Donor 2 | Line 3 | bac/ann | 12 | 10 | 0 | CT | CT | AG | TT | CC | GG | AA | TT |
| BCMS Family Donor 2 | Line 3 | ann/ann | 10 | 0 | 5 | TT | TT | GG | TT | CC | GG | AA | TT |
| BCMS Family Donor 2 | Line 4 | bac/ann | 38 | 29 | 0 | CT | CT | AG | TT | CC | GG | AA | TT |
| BCMS Family Donor 2 | Line 4 | ann/ann | 26 | 0 | 13 | TT | TT | GG | TT | CC | GG | AA | TT |
| CMS Donor 3 = Pl497974 | | | | | | TT | TT | GG | TT | CC | GG | AA | TT |
| Recurrent Parent | | | | | | CC | CC | AA | CC | GG | AA | TT | AA |
| BCMS Family Donor 3 | Line 1 | bac/ann | 0 | — | — | — | — | — | — | — | — | — | — |
| BCMS Family Donor 3 | Line 1 | ann/ann | 78 | 0 | 28 | TT | TT | GG | TT | CC | GG | AA | TT |
| BCMS Family Donor 3 | Line 2 | bac/ann | 0 | — | — | — | — | — | — | — | — | — | — |
| BCMS Family Donor 3 | Line 2 | ann/ann | 51 | 0 | 19 | TT | TT | GG | TT | CC | GG | AA | TT |
| BCMS Family Donor 3 | Line 3 | bac/ann | 0 | — | — | — | — | — | — | — | — | — | — |
| BCMS Family Donor 3 | Line 3 | ann/ann | 81 | 0 | 25 | TT | TT | GG | TT | CC | GG | AA | TT |
| BCMS Family Donor 3 | Line 4 | bac/ann | 0 | — | — | — | — | — | — | — | — | — | — |
| BCMS Family Donor 3 | Line 4 | ann/ann | 81 | 0 | 18 | TT | TT | GG | TT | CC | GG | AA | TT |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A *Capsicum annuum* plant comprising a chromosomal segment from *Capsicum baccatum* on chromosome 6, wherein said chromosomal segment comprises an allele that confers female fertility in a male sterile *Capsicum annuum* plant having a *Capsicum baccatum* cytoplasm relative to a plant lacking said chromosomal segment, wherein said chromosomal segment is flanked by Marker M7 (SEQ ID NO: 7) and Marker M17 (SEQ ID NO: 17) in said plant.

2. The plant of claim 1, wherein said chromosomal segment is further defined as located between 428,143 bp and 3,500,133 bp on the public pepper CM334 v1.55 map.

3. A seed that produces the plant of claim 1.

4. A plant part of the plant of claim 1.

5. The plant part of claim 4, wherein the plant part is a cell, a seed, a root, a stem, a leaf, a flower, a fruit, or pollen.

6. A method for producing a *Capsicum annuum* plant that confers uniform female fertility in a male sterile *Capsicum annuum* plant having a *Capsicum baccatum* cytoplasm, comprising introgressing into said plant a chromosomal segment from *Capsicum baccatum* on chromosome 6 that confers uniform female fertility in a male sterile *Capsicum annuum* plant having a *Capsicum baccatum* cytoplasm relative to a plant lacking said chromosomal segment, and wherein said chromosomal segment is flanked by Marker M7 (SEQ ID NO: 7) and Marker M17 (SEQ ID NO: 17).

7. The method of claim 6, wherein said introgressing comprises:

a) crossing a plant comprising said chromosomal segment with itself or with a second *Capsicum annuum* plant of a different genotype to produce one or more progeny plants; and b) selecting a progeny plant comprising said chromosomal segment.

8. The method of claim 7, wherein the progeny plant is an $F_2$-$F_6$ progeny plant, and wherein said progeny plant comprises said chromosomal segment.

9. The method of claim 7, wherein said crossing comprises backcrossing.

10. The method of claim 9, wherein said backcrossing comprises from 2-7 generations of backcrosses.

11. A *Capsicum annuum* plant produced by the method of claim 7, wherein said plant comprises said chromosomal segment.

12. A method of producing food or feed comprising obtaining a plant according to claim 1, or a part thereof, and producing said food or feed from said plant or part thereof.

13. A *Capsicum annuum* plant obtainable by a method comprising the step of introgressing into a plant a uniform female fertility phenotype allele from *Capsicum baccatum*, wherein said uniform female fertility phenotype allele is defined as located in a chromosomal segment flanked by Marker M7 (SEQ ID NO: 7) and Marker M17 (SEQ ID NO: 17).

14. The *Capsicum annuum* plant of claim 13, wherein said introgressing comprises backcrossing or marker-assisted selection.

15. A method of selecting a *Capsicum annuum* plant exhibiting uniform female fertility, comprising:

a) crossing the *Capsicum annuum* plant of claim 1 with itself or with a second *Capsicum annuum* plant of a different genotype to produce one or more progeny plants; and b) selecting a progeny plant comprising said chromosomal segment.

16. The method of claim 15, wherein selecting said progeny plant comprises identifying a genetic marker genetically linked to said chromosomal segment.

17. The method of claim 16, wherein selecting said progeny plant comprises identifying a genetic marker within or genetically linked to said chromosomal segment flanked in the genome of said plant by Marker M7 (SEQ ID NO: 7) and Marker M17 (SEQ ID NO: 17) on chromosome 6.

18. The method of claim 15, wherein said progeny plant is an $F_2$-$F_6$ progeny plant, and wherein said progeny plant comprises said chromosomal segment.

19. The method of claim 15, wherein producing said progeny plant comprises backcrossing.

20. The *Capsicum annuum* plant of claim 1, wherein said plant has a cytoplasmic male sterility phenotype.

21. The plant of claim 20, wherein the cytoplasmic male sterility phenotype is defined as *Baccatum* cytoplasmic male sterility.

* * * * *

UNITED STATES PATENT AND TRADEMARK OFFICE
CERTIFICATE OF CORRECTION

| | |
|---|---|
| PATENT NO. | : 11,516,987 B2 |
| APPLICATION NO. | : 16/453748 |
| DATED | : December 6, 2022 |
| INVENTOR(S) | : Eckard et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 121 days.

Signed and Sealed this
Fourteenth Day of January, 2025

Derrick Brent
*Acting Director of the United States Patent and Trademark Office*